US009585977B2

(12) United States Patent
Zumeris et al.

(10) Patent No.: US 9,585,977 B2
(45) Date of Patent: Mar. 7, 2017

(54) SYSTEM AND METHOD FOR SURFACE ACOUSTIC WAVE TREATMENT OF SKIN

(75) Inventors: Jona Zumeris, Haifa (IL); Harold Jacob, Cedarhurst, NY (US); Hanan Raskin, Kfar Saba (IL); Gera Kratysh, Haifa (IL); Yanina Zumeris, Haifa (IL)

(73) Assignee: NANOVIBRONIX, INC, Cedarhurst, NY (US)

( * ) Notice: Subject to any disclaimer, the term of this patent is extended or adjusted under 35 U.S.C. 154(b) by 2367 days.

(21) Appl. No.: 11/710,615

(22) Filed: Feb. 26, 2007

(65) Prior Publication Data
US 2007/0232962 A1    Oct. 4, 2007

Related U.S. Application Data

(60) Provisional application No. 60/776,067, filed on Feb. 24, 2006.

(51) Int. Cl.
*A61H 1/00* (2006.01)
*A61L 2/025* (2006.01)
(Continued)

(52) U.S. Cl.
CPC .......... *A61L 2/025* (2013.01); *A61H 23/0236* (2013.01); *A61L 2/24* (2013.01);
(Continued)

(58) Field of Classification Search
CPC .......... A61H 2201/105; A61H 23/0236; A61L 2/025; A61L 2/24; A61M 2025/0019
(Continued)

(56) References Cited

U.S. PATENT DOCUMENTS 3,427,481 A * 2/1969 Colbert ................ B06B 1/0685
                                                        310/327
4,040,414 A   8/1977 Suroff
(Continued)

FOREIGN PATENT DOCUMENTS

WO    WO 03/099100 A2 * 12/2003
WO    WO 03099100      12/2003
WO    WO 2005/117156   12/2005

OTHER PUBLICATIONS

Miyasaka et al (Ultrasonic Tissue Characterization of Photodamaged Skin by Scanning Acoustic Microscopy, Tokai J Exp Clin Med, vol. 30, No. 4, pp. 217-225, 2005.*
(Continued)

*Primary Examiner* — James Kish
*Assistant Examiner* — Saurel J Selkin
(74) *Attorney, Agent, or Firm* — Mark S. Cohen; Pearl Cohen; Zedek Latzer Baratz LLP

(57) ABSTRACT

Methods and devices for treating skin include a skin-contacting portion, an actuator and a processor, wherein activation of the actuator causes surface acoustic waves of Rayleigh, "pseudo" Rayleigh types to be produced on the skin around the actuator. In a location which is under the actuator, the actuator produces tension and repulsion of skin particles. These surface acoustic waves can be used to provide treatment to the skin, including wound healing, non-adhesion of bandages, reduced infection, reduced pain and cosmetic enhancements. The skin-contacting portion may be a patch or bandage, a glove, a hand-held device, or any other suitable configuration. The actuator is incorporated into the skin-contacting portion.

34 Claims, 19 Drawing Sheets

(51) Int. Cl.
*A61H 23/02* (2006.01)
*A61L 2/24* (2006.01)
*A61M 25/00* (2006.01)

(52) U.S. Cl.
CPC .............. *A61H 2201/105* (2013.01); *A61M 2025/0019* (2013.01)

(58) Field of Classification Search
USPC .......................................................... 601/2
See application file for complete search history.

(56) References Cited

U.S. PATENT DOCUMENTS

| | | | |
|---|---|---|---|
| 4,419,248 A | 12/1983 | Costerton | |
| 5,200,665 A * | 4/1993 | Iijima | H02N 2/103 310/317 |
| 5,312,813 A | 5/1994 | Costerton et al. | |
| 5,366,505 A | 11/1994 | Farber | |
| 5,462,644 A | 10/1995 | Woodson | |
| 5,505,945 A | 4/1996 | Gristina et al. | |
| 5,636,180 A | 6/1997 | Grothaus et al. | |
| 5,876,602 A | 3/1999 | Jons et al. | |
| 5,895,362 A * | 4/1999 | Elstrom et al. | 600/573 |
| 5,954,977 A | 9/1999 | Miller et al. | |
| 6,086,772 A | 7/2000 | Tanimura et al. | |
| 6,096,225 A | 8/2000 | Yang et al. | |
| 6,156,549 A | 12/2000 | Drewes et al. | |
| 6,326,177 B1 | 12/2001 | Schoenbach et al. | |
| 6,428,477 B1 * | 8/2002 | Mason | 600/437 |
| 6,433,244 B1 * | 8/2002 | Roe et al. | 604/361 |
| 7,165,451 B1 | 1/2007 | Brooks et al. | |
| 7,429,248 B1 * | 9/2008 | Winder et al. | 601/2 |
| 2002/0068866 A1 | 6/2002 | Zikorus et al. | |
| 2003/0083599 A1 * | 5/2003 | Kitov | A61H 23/0236 601/84 |
| 2003/0177819 A1 | 9/2003 | Maale | |
| 2003/0236487 A1 | 12/2003 | Knowlton | |
| 2004/0027034 A1 | 2/2004 | Kawaguchi et al. | |
| 2004/0073267 A1 | 4/2004 | Holzer | |
| 2004/0236268 A1 | 11/2004 | Mitragotri et al. | |
| 2004/0236269 A1 * | 11/2004 | Marchitto et al. | 604/22 |
| 2005/0038376 A1 | 2/2005 | Zumeris et al. | |
| 2005/0075599 A1 * | 4/2005 | Redding, Jr. | 604/22 |
| 2005/0095351 A1 | 5/2005 | Zumeris et al. | |
| 2005/0137656 A1 | 6/2005 | Malak | |
| 2005/0200434 A1 * | 9/2005 | Takano | 333/193 |
| 2005/0267451 A1 | 12/2005 | Black | |
| 2005/0268921 A1 | 12/2005 | Zumeris et al. | |
| 2005/0283110 A1 | 12/2005 | Atala et al. | |
| 2006/0184071 A1 * | 8/2006 | Klopotek | 601/2 |
| 2007/0038156 A1 * | 2/2007 | Rosenberg | 601/2 |

OTHER PUBLICATIONS

International Search Report for International Application No. PCT/US07/04849, mailed Feb. 6, 2008.

International Search Report from International Application No. PCT/US07/04842, mailed Jun. 10, 2008.
Office Action in U.S. Appl. No. 11/710,616, dated Jan. 22, 2010.
U.S. Appl. No. 11/710,616, Feb. 26, 2007, Zumeris et al.
Maki DG, Tambyah PA; "Engineering Out the Risk of Infection with Urinary Catheters". Emerging Infectious Diseases; vol. 7, p. 1-6, 2001.
Gristina AG, "Biomaterial-Centered Infection: Microbial Adhesion Versus Tissue Intergration". Science 1987, 237: 1588-1595.
Schierholz JM and Beuth J. "Implant Infections: a Haven for Opportunistic Bacteria". 2001. J. Hosp. Infect. 49: 87-93.
Whiteley, M., Lee, K. M. & Greenberg, E. P. "Identification of Genes Controlled by Quorum Sensing in *Pseudomonas aeruginosa*". Proc. Natl Acad. Sci. USA 96, 13904-13909 (1999).
Lewis K. "Riddle of Biofilm Resistance. Antimicrob. Agents Chemother". 2001, 45, 999-1007.
Mahenthiralingam E., Campbell ME., Speed DP. "Nonmotility and Phagocytic Resistance of Pseudomonas aeruginosa Isolates from Chronically Colonized Patients with Cystic Fibrosis". Infect Immun. 1994, 62:596-605.
Thibon P., Le Coutour X., Leroyer R., Fabry J. Randomized Multi-Centre Trial of the Effects of a Catheter Coated with Hydrogel and Silver Salts on the Incidence of Hospital-Acquired Urinary Tract Infections.J. Hosp Infect. (2000) 45:117-1124.
Yamamoto AJ, Solomon JA, Soulen MC, Tang J, Parkinson K, Lin R, Schears GJ. "Sutureless Securement Device Reduces Complications of Peripherally Inserted Central Venous Catheters". J. Vasc Intery Radiol. 2002;13:77-81.
Rediske AM, Roeder BL, Nelson JL et al. "Pulsed Ultrasound Enhances the Killing of *Escherichia coli* Biofilms by Aminoglycoside Antibiotics in Vivo". Antimicrobial Agents and Chemotherapy, Mar. 2000, p. 771-772.
Carmen JC, Roeder BL, Nelson JL, Ogilvie RL, Robison RA, Schaalje GB, Pitt WG. "Treatment of Biofilm Infections on Implants with Low-Frequency Ultrasound and Antibiotics" .Am J Infect Control. 2005, 33:78-82.
Schachter B. "Slimy Business—the Biotechnology of Biofilms", Nature Biothechnology, Apr. 2003; 21:361-365.
Trautner BW, Darouich RO, "Catheter Associated Infections Pathogenesis Affect Prevention", Archives of Internal Medicine, Apr. 2004; 164:842-850.
King D. "Diagnostic Ultrasound" Physical and Technical Principles p. 26-27, 1974.
Donlan R. "Biofilms: microbial life on surfaces" Emerging Infectious Diseases vol. 8, No. 9, p. 881-890, 2002.
Campbell C. "Surface Acoustic Wave Devices for Mobile and Wireless Communications" Academic Press Inc. p. 19-22, 1998.
Ueha S. et al. "Ultrasonic Motors Theory and Applications" Clarendon Press Oxford 1993.
Final of Action for U.S. Appl. No. 11/710,616, dated Sep. 13, 2010.
Office Action for Chinese Application No. 200780014875.5, dated Sep. 8, 2010.
Supplementary European Search Report for corresponding European Application No. EP 07861247 mailed Aug. 2, 2012.

* cited by examiner

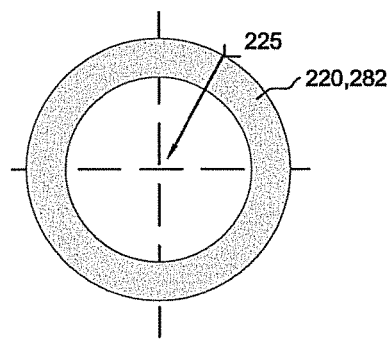
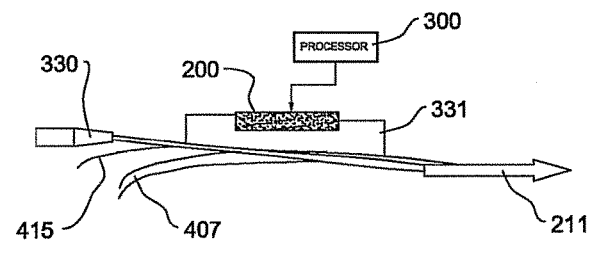
Fig.14B    Fig.15
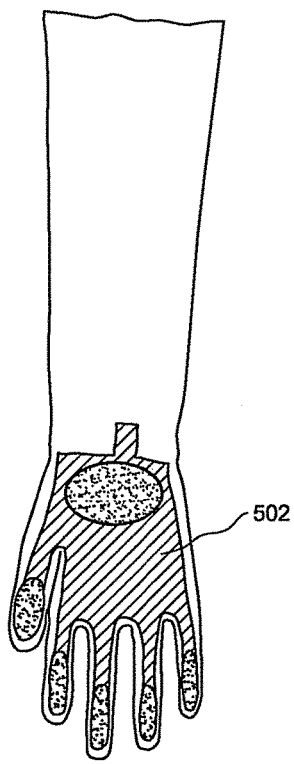
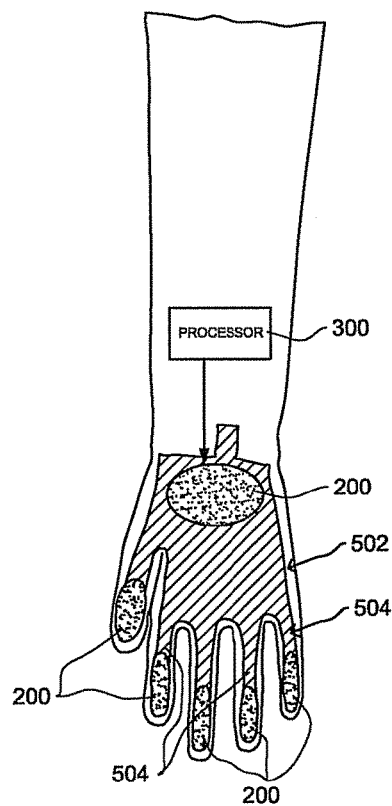
Fig.16A    Fig.16B

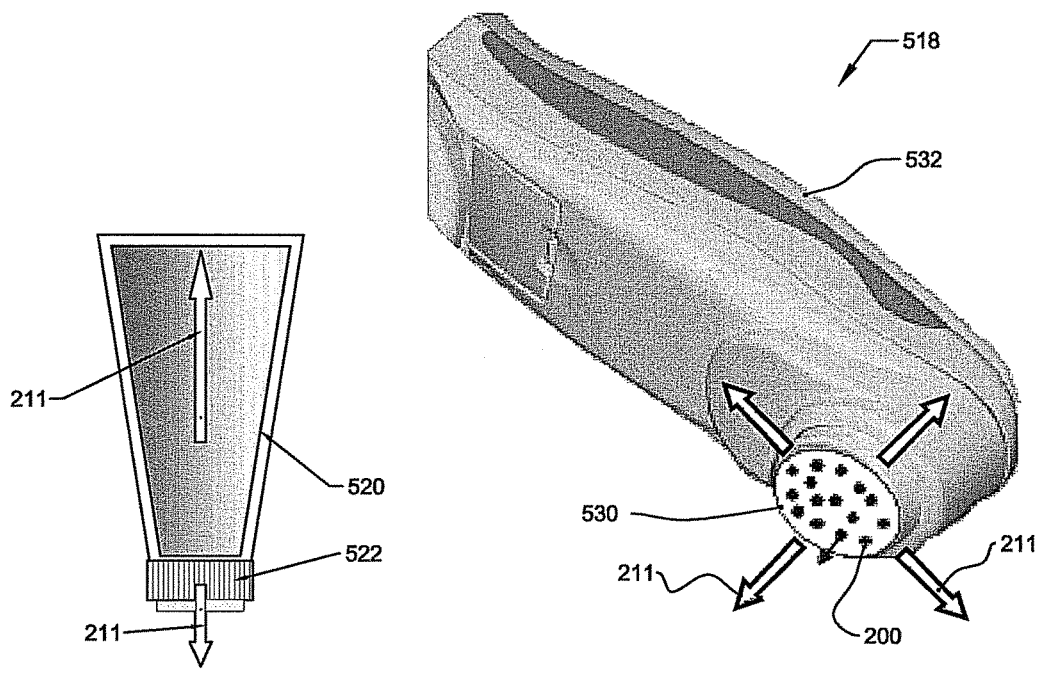
Fig.39
Fig.38
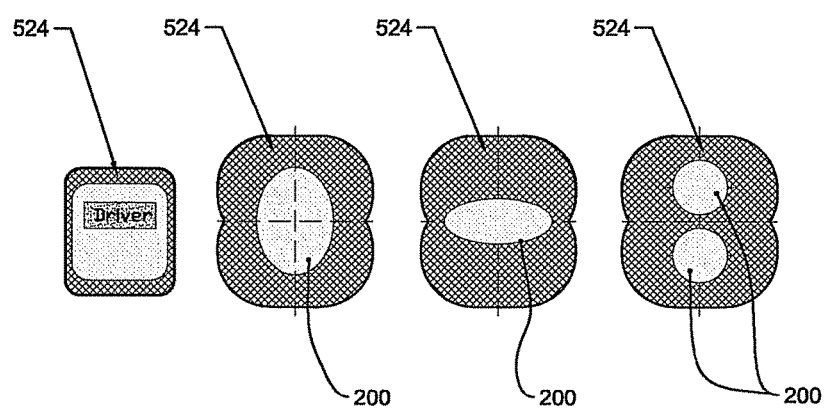
Fig.40

SYSTEM AND METHOD FOR SURFACE ACOUSTIC WAVE TREATMENT OF SKIN

CROSS REFERENCE TO RELATED APPLICATIONS

This application claims the benefit of U.S. Provisional Application Ser. No. 60/776,067, filed on Feb. 24, 2006, which is incorporated in its entirety herein by reference.

FIELD OF THE INVENTION

The present invention relates to the methods and devices creating surface acoustic waves on human skin surfaces and directing them to particular places of interest for therapeutic needs, wound healing, disinfecting and anti-agent applications.

BACKGROUND OF THE INVENTION

Ultrasonic waves have been widely used in medical applications, including diagnostics and therapy, and in many industrial applications, for welding, cutting, fiber optics technology, speed meters, etc. Diagnostic use of ultrasound waves includes using ultrasonic waves to detect underlying structures in an object or human body. An ultrasonic transducer is placed in contact with the tissue or object via a coupling medium, and high frequency (1-10 MHz) ultrasonic waves are directed to the tissue. Upon contact with the various underlying structures, the waves are reflected back to a receiver adjacent the transducer. By comparison of the signals of the ultrasonic waves sent with the reflected ultrasonic wave as received, an image of the underlying structure can be produced.

Three therapeutic medical uses of ultrasound waves include aerosol mist production, contact physiotherapy, and soft tissue ablation. The ultrasound contact physiotherapy procedure may cause a patient significant discomfort and/or pain, and skin may appear raw and damaged.

However, the necessity of direct contact with or without a coupling medium makes current methods undesirable. Some tissue conditions may be accessible to contact ultrasound devices but would be impractical for contact ultrasound treatment. For example, fresh or open wounds resulting from trauma, burns, surgical interventions are not suitable for direct contact ultrasound treatment because of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface. In general, conventional ultrasound therapy considers applicator placed on the skin and deep propagation of ultrasonic waves and much of the energy is wasted.

SUMMARY OF THE INVENTION

According to one aspect of the invention there is provided a method for treating human skin. The method includes positioning an actuator on the skin, electrically connecting the actuator to a processor, activating the actuator via the processor, producing surface acoustic waves on the skin based on the activating, and controlling parameters of the activating so as to achieve particular treatment effects on the skin by the produced surface acoustic waves.

According to another aspect of the invention, there is provided a device for treatment of skin. The device includes a skin-contacting portion, an actuator incorporated into the skin-contacting portion, the actuator for producing surface acoustic waves on the skin, and a processor for controlling the actuator.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which:

FIG. 14B is an illustration of a ring-shaped piezo-element used in the embodiment of FIG. 14A;

FIG. 15 is a schematic illustration of an acoustic pad placed on skin, in accordance with embodiments of the present invention;

FIGS. 16A and 16B are illustrations of an acoustic glove in accordance with embodiments of the present invention;

FIG. 38 is an illustration of a hand-held cosmetic device, in accordance with embodiments of the present invention;

FIG. 39 is an illustration of a tube of cream having SAW characteristics; and FIG. 40 is an illustration of active pain relief patches, in embodiments of the present invention.

Figure 1A:
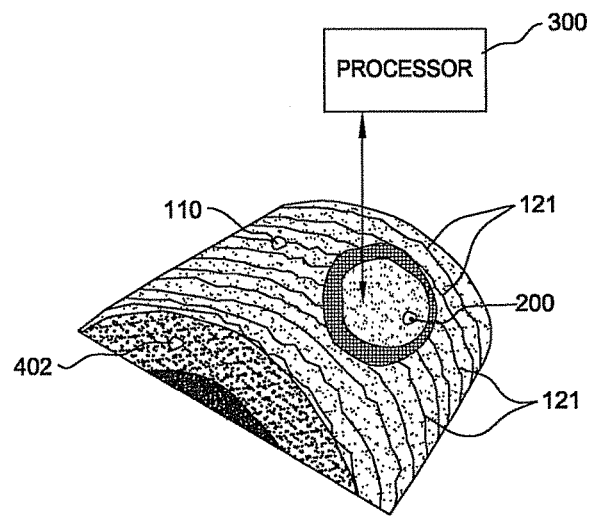
FIG. 1A is a schematic illustration of an actuator for producing surface acoustic waves positioned on an external surface of a portion of skin, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention. The present invention is directed to methods for treating the surfaces of human skin and underlying layers with surface acoustic waves (SAW) of Rayleigh, "pseudo" Rayleigh, or Lamb type. Specifically, the present invention can be used to achieve rejuvenation, local improvement of the blood circulation, heating of the tissue, accelerated enzyme activity, muscle relaxation, pain reduction, and enhancement of natural healing processes.

The term "wound" for the purposes of "wound healing", as used throughout the present application, includes ulcers such as venous ulcers as well as burns, ulcerated wounds due to, for example, diabetes, surgical incisions or other surgical cuttings including stitched surgical cuttings, skin grafts, hair transplants, re-vascularization, bed sores, tissue dehiscence, and ligament and tendon repair and reconstruction. In general, as used throughout the present disclosure, the term "wound healing" encompasses addressing damage to, repair of, or restoration of soft tissue.

The principles and steps of methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

1. Basic Principles

Conventional ultrasound used for therapy may be of high frequency (1-4 MHz) and low frequency (20-120 KHz), and may have longitudinal or transverse characteristics. The present application discloses excitement of surface acoustic waves on the skin (low-power, low-frequency) and employment of this phenomenon for therapeutic needs. Our theoretical constructions and experimental results proved that low-power, low-frequency ultrasound (20-120 kHz, 0.05-1.0 W/cm$^2$) propagated in the form of surface acoustic waves is effective in one or more of the following: inhibiting adhesion, micro-massage, healing processes, tissue fluid interchange, increased growth of capillary, increased pH of tissue liquids, lowered pain syndrome, resistance of thrombus formation, better drug administering, reduced friction, the cleansing of tissue, the removal of necrotic debris, disinfection, the "biostimulation" of cells, blood flow, micromassaging, drying, intensity of drug diffusion, activeness of the coating agents, and wound healing.

Reference is now made to FIG. 1A, which is a schematic illustration of an actuator 200 for producing surface acoustic waves positioned on an external surface 110 of a portion of skin 402, in accordance with embodiments of the present invention. Actuator 200 is in electrical communication with a processor 300. Processor 300 may be, for example, a central processing unit (CPU), and may include an oscillator, an amplifier, and any other component used for receiving and transmitting signals and making calculations related to the received and transmitted signals. Upon receipt of an electrical signal from processor 300, actuator 200 is capable of generating high frequency mechanical vibrations, in a range from KHz to MHz. These high frequency mechanical vibrations create surface acoustic waves (SAW) 121 (in the nanometer range) on external surface 110 of skin 402, and also penetrate into some of the deeper layers of skin 402, as will be described in further detail hereinbelow. The frequency of generated mechanical oscillations in actuator 200 is directly related to the frequency produced by processor 300. Thus, for example, if oscillations are in the MHz range, the mechanical vibrations will also be in the MHz range, and similarly for other ranges. The energy source applied via processor 300 may have a periodical or non-periodical character, and may be electromechanical, electromagnetic, or electro-optical.

Actuator 200 may be comprised of one or multiple piezoelectric transducers, one or more electromagnetic acoustic transducers, or one or multiple laser pulse transducers. In the case of piezoelectric and electromagnetic transducers, direct contact between actuator 200 and skin 402 is necessary. In the case of laser pulse transducers, non-contact methods may be employed.

The term "surface acoustic waves" (SAW) as used throughout the present disclosure, includes several types of waves or combinations thereof, as follows:
Surface—Rayleigh (elliptical orbit—symmetrical mode)
Plate Wave—Lamb—component perpendicular to surface (extensional wave)
Plate Wave—Love—parallel to plane layer, perpendicular to wave direction
Stoneley (Leaky Rayleigh Waves)—wave guided along interface
Sezawa—antisymmetric mode Surface or Rayleigh waves travel along the boundary between two different media, penetrating to a depth of about one wavelength. The particle movement has an elliptical orbit. Lamb wave is a special case of Rayleigh waves, which occurs when the material is relatively thin.

Figure 1B:
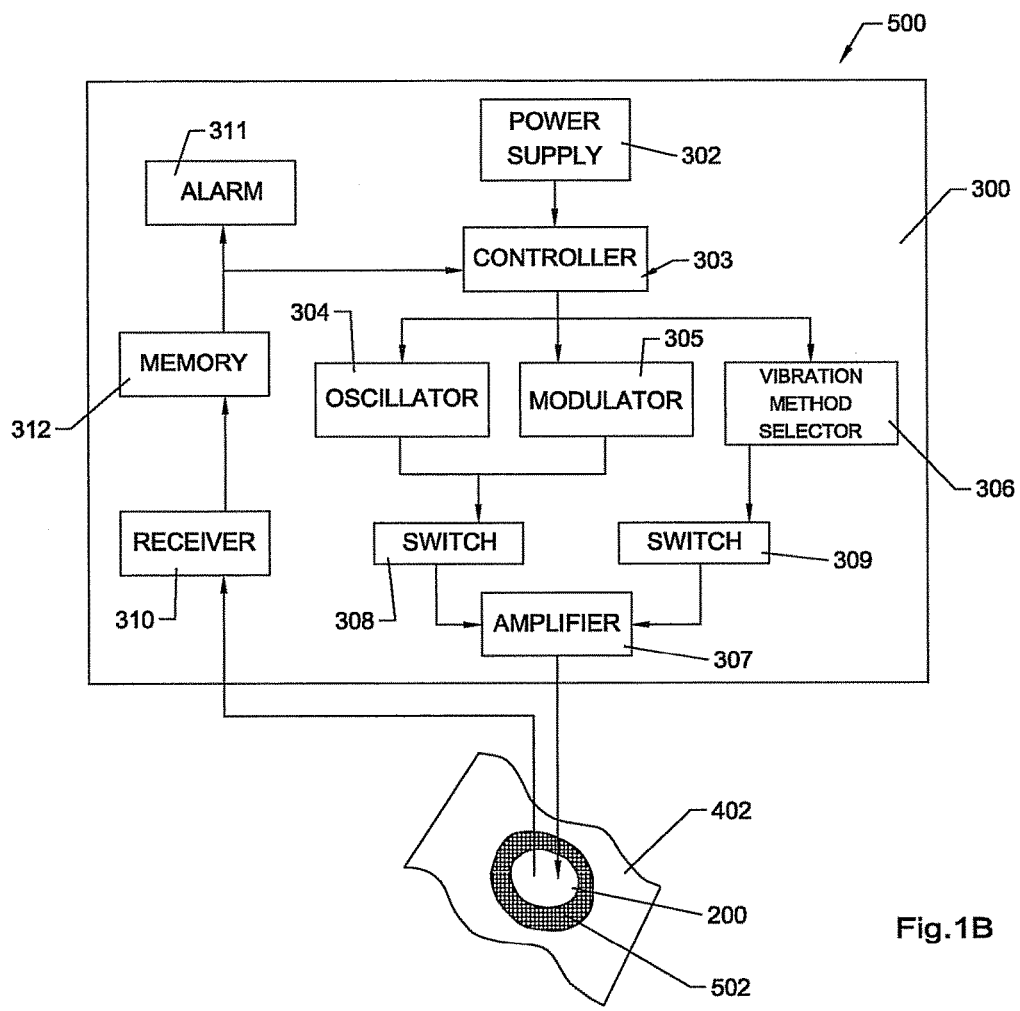
FIG. 1B is a block diagram illustration of a system for treating skin using SAW, in accordance with embodiments of the present invention.

Reference is now made to FIG. 1B, which is a block diagram illustration of a system 500 for treating skin using surface acoustic waves (SAW), in accordance with embodiments of the present invention. The system shown herein is useful in creating SAW via a piezoelectric actuator. However, as noted below, other methods may be used to create SAW as well, including electromagnetic stimulation and laser pulse excitation. System 500 includes an actuator 200, a processor 300 in electrical communication with actuator 200, and optionally a coupler 502 positioned between actuator 200 and skin 402. In the embodiment shown herein, actuator 200 is a piezoelectric actuator, and works by converting electrical signals from processor 300 into mechanical energy, wherein the mechanical energy is transmitted to skin 402 and creates SAW on surfaces thereof. In some embodiments, actuator 200 is configured to transmit electrical signals proportional to the mechanical energy created to processor 300, and may thus provide a feedback loop to regulate the electrical signals produced by processor 300. Coupler 502 may optionally be placed between actuator 200 and skin 402 in order to match acoustic signal transmission properties of materials of skin 402 and actuator 200.

Processor 300 includes a power supply 302 for providing electrical energy to system 500. In some embodiments, power supply 302 is a separate unit (such as a power cord), and in some embodiments, power supply 302 is incorporated into processor 300 (such as a battery). Processor 300 further includes a controller 303 for controlling output parameters of processor 300. Controller 303 is in electrical communication with an oscillator 304 for providing signals at various frequencies, a modulator 305 for modulating parameters such as frequency, amplitude, etc., and a vibration method selector 306 for providing different types of vibrations, such as single-phase, two-phase or multi-phase vibrations. Oscillator 304 and modulator 305 are connected to a first switch 308, for selection of signal parameters. Vibration method selector 306 is connected to a second switch 309 for selection of vibration method. The selected signal of the selected vibration type is sent through an amplifier 307 to actuator 200.

For embodiments wherein electrical signals are sent from actuator 200 to processor 300, these signals are received by a receiver 310 within processor 300. It should be noted that in some instances, signals are sent by a separate sensor placed on or near or incorporated within actuator 200, as will be described in further detail hereinbelow. Signals received by receiver 310 are sent to a memory module 312, where they are compared with expected values. Results of the comparison are then either sent to controller 303, where signal parameters such as amplitude and frequency may be automatically adjusted based on the received information, or sent to an alarm 311 for alerting a user that parameters should be adjusted manually.

Selection of parameters depends on the use and application of system 500, and may vary according to specific requirements. For example, when actuator 200 is applied directly to the skin, frequencies may be in a range of 0.1 Hz-10 MHz. When an interface is present, such as a cream, drug, wound dressing or the like, frequencies may be in a range of 1 KHz-20 KHz so as to provide higher energy waves that can penetrate the interface. Alternatively, higher energy may be accomplished by modulation of waves to produce increased amplitudes. Pulsed or continuous inputs may be used. In addition, depending on the treatment the types of waves may differ as well. For example, acne may be treated by focused waves, as will be described in further detail hereinbelow, while micro-massage may be accomplished via a large range of wave types. Microstreaming may also be accomplished via a large range of wave types; however, the speed of microstreaming may vary based on the chosen parameters. Speed of microstreaming may be in a range of 1 nm/minute to 10 microns/minute.

Figure 2:
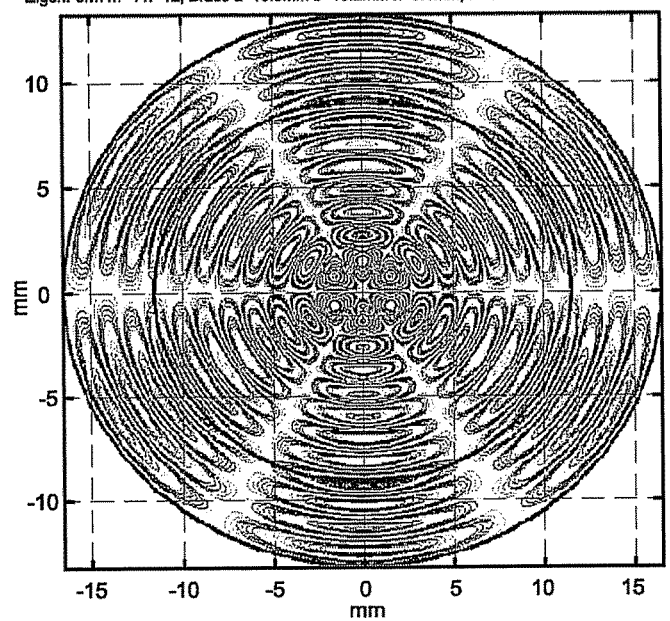
FIG. 2 is a diagrammatic illustration of energy distribution on a disk-shaped piezoelectric plate, which in some embodiments may serve as an actuator of the system of FIG. 1B.

Reference is now made to FIG. 2, which is a diagrammatic illustration of energy distribution on a disk-shaped piezoelectric plate, which in some embodiments may serve as actuator 200. It is seen that multiple energy picks (about 48 are shown) interchange with minimal energy levels on the actuator surface, acting like small energy needles. These energy changes produce tension and repulsion of the skin particles beyond the active plate resulting in different therapeutic effects. Furthermore, due to these energy picks, "small vibrating needles" actuator 200 creates surface acoustic waves which in the form of running waves are transmitted to the areas around the actuator. Different energy penetration depths to the skin layers may be achieved because different energy picks on the surface of the plate may be excited changing one or more: the energy level of the driver, piezo element excitement frequency, vibration characteristics m and n (as will discussed with regard to FIGS. 7 and 8).

Figure 3A:
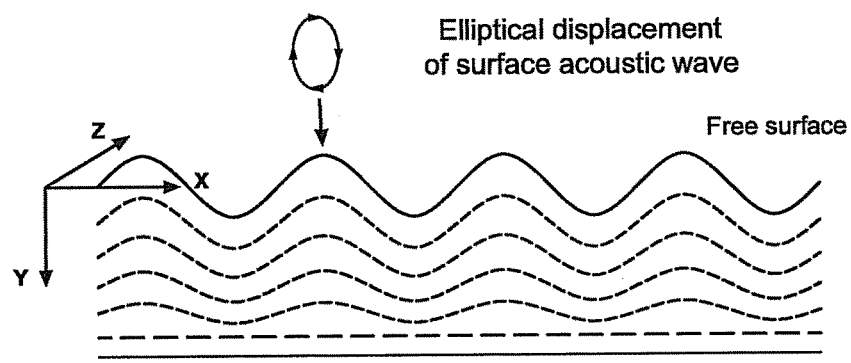
FIG. 3A is a schematic representation showing the propagation of a Rayleigh wave on an elastic surface.

Reference is now made to FIG. 3A, which is a schematic representation (not to scale) showing the propagation of a Rayleigh wave on an elastic surface. As shown in FIG. 3A, the physical motion of this "true-SAW" wave type is associated with mechanically time-dependent elliptical displacement of the surface structure. One component of the physical displacement is parallel to the SAW propagation axis X, and another component is normal to the surface along axis Y.

In general, the amplitude of surface displacement along the y-axis is larger than along the SAW propagation axis X. The amplitudes of both SAW displacement components are negligible for penetration depths (into the body of the solid, such as, for example skin 402) greater than a few acoustic wavelengths.

Propagation of Lamb waves depends on density, elastic, and other material properties of the solid (such as skin 402, for example), and they are influenced a great deal by selected frequency and material thickness. With Lamb waves, a number of modes of particle vibration are possible, but the two most common are symmetrical and antisymmetrical. The complex motion of the particles is similar to the elliptical orbits for surface waves.

Figure 3B:
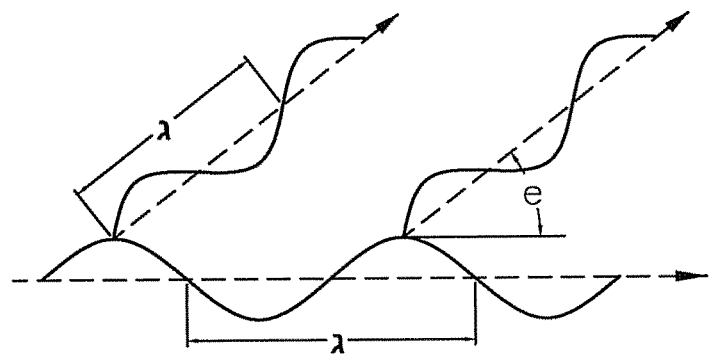
FIG. 3B is a schematic illustration showing the generation of a compressional wave into fluid by a SAW having a wavelength $\lambda$ and delivered at an angle $\xi$ to an external surface of skin.

Reference is now made to FIG. 3B, which is a schematic illustration showing the generation of a compressional wave into fluid $\lambda_1$ by a SAW having a wavelength $\lambda$ and delivered at an angle $\xi$ to external surface 110 of skin 402. Pressure (gas or fluid loading) also contributes to acoustic wave attenuation and velocity change. In this case, attenuation is due to the generation of compressional waves in the gas or fluid in contact with a surface of skin 402. Thus, the shear vertical component of the wave causes periodic compression and rarefaction of the gas or fluid, resulting in a coupling of acoustic energy from skin 402 into the gas or fluid. The condition for this to occur is:

$$\cos \text{angle } \xi = \lambda/\lambda_1$$

The presence of SAW on internal and external surfaces 120 and 110 of skin 402 causes a pushing/pulling effect of materials on these surfaces, including fluids and particulates suspended therein. Thus, in the case of formation of a biofilm, the SAW may reduce the existing biofilm, augment and enhance the effect of antibiotics on the biofilm (i.e. decrease the biofilm's resistance to antibiotics), produce antimicrobial and antithrombogenic surfaces, and augment tissue therapy.

There are several methods for producing SAW on skin, including electromagnetic, laser pulses, or piezoelectric methods, as will be discussed in greater detail hereinbelow.

Electromagnetic Transducers

Figure 4:
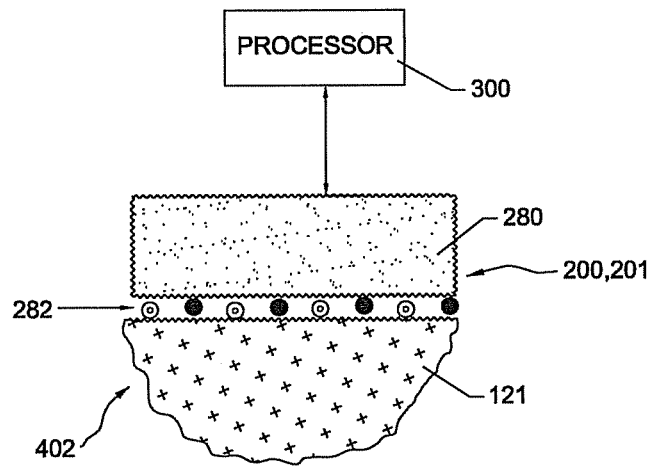
FIG. 4 is a cross-sectional illustration of skin with an actuator attached thereto, wherein the actuator is comprised of an electromagnetic transducer.

Reference is now made to FIG. 4, which is a cross-sectional illustration of a skin 402 with an actuator 200 attached thereto, wherein actuator 200 is comprised of an electromagnetic transducer 201. As shown in FIG. 4, actuator 200 is comprised of a base portion 280 and an activating portion 282. Base portion 280 may be of any conductive material, such as a metal and activating portion 282 is comprised of electromagnetic transducers, such as electromagnetic ultrasound transducers available from Olympus company, Panametrics-NDT Ultrasonic Transducer. Base portion 280 may be the face of electromagnetic transducer. We may get the SAW in the desired range, by choosing the frequency of the electromagnetic transducer.

Activating portion 282 is configured to excite Lamb waves in plates. This type of actuator vibrates the atoms within skin 402. Processor 300 is in electrical communication with base portion 280. Processor 300 applies a current to base portion 280, which is comprised of an electrically conductive material. When the current is applied at a particular ultrasonic frequency activating portion 282 creates vibrations of Lamb wave type, wherein the distance between max amplitudes will be equal to one-half the wavelength of SAW excited on the skin.

Pulsed Laser Transducers

Figure 5:
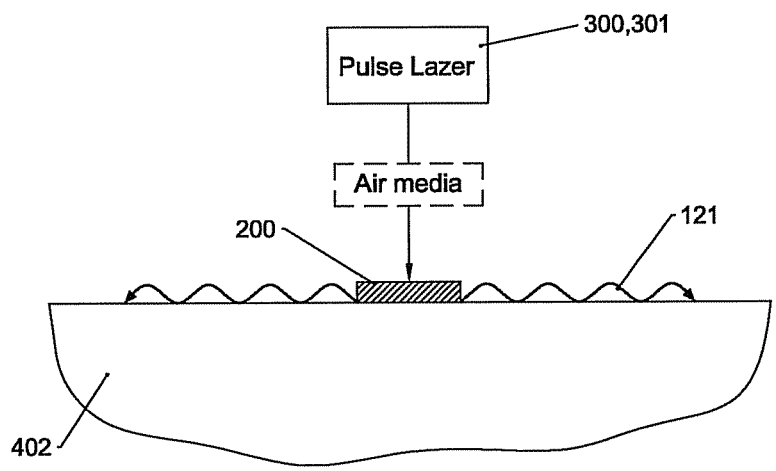
FIG. 5 is a diagrammatic illustration of skin with a processor, wherein the processor is a pulsed laser device.

Reference is now made to FIG. 5, which is a diagrammatic illustration of skin 402 with a processor 300, wherein processor 300 is a pulsed laser device 301. Actuator 200 is a metallic plate which is configured to vibrate in response to laser pulses from processor 300. No contact is necessary between actuator 200 and processor 200 since laser pulses travel through the air. Pulsed laser device 301 is used to generate SAW 121 in solids by a thermoelastic mechanism, wherein the resulting elastic displacement waveform has a wide band.

The frequency range of the SAW excited using pulsed lasers has limited bandwidth as only short pulse widths may be excited with pulsed laser device 301 in a solid. The amplitude and the frequency bandwidth of the laser-induced SAW are improved by decreasing the radius of the focused laser spot. For example, laser pulse focused to a line produced by Max-Planck-Institute for Solid State Research may be applied.

Piezo-Electric Transducers

Actuator 200 may include one or more piezo-actuators 203, which are configured to provide SAW in accordance with embodiments of the present invention. These piezo-actuators 203 are configured to provide vibrations at amplitudes of between 0.2-2 nanometers.

Figure 6A:
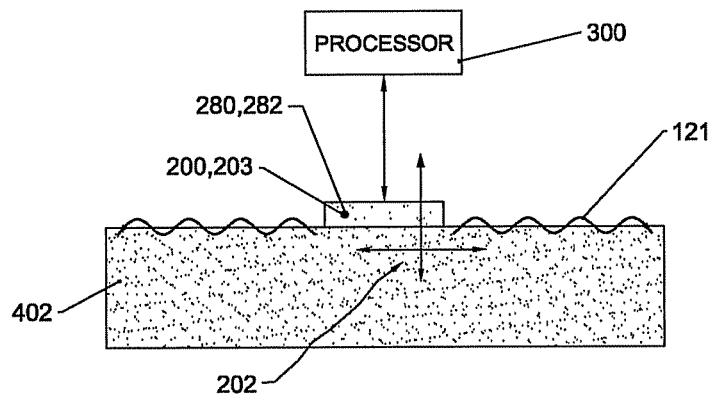
FIGS. 6A-6C are illustrations of an actuator comprised of one or multiple piezo-elements.
Figure 6B:
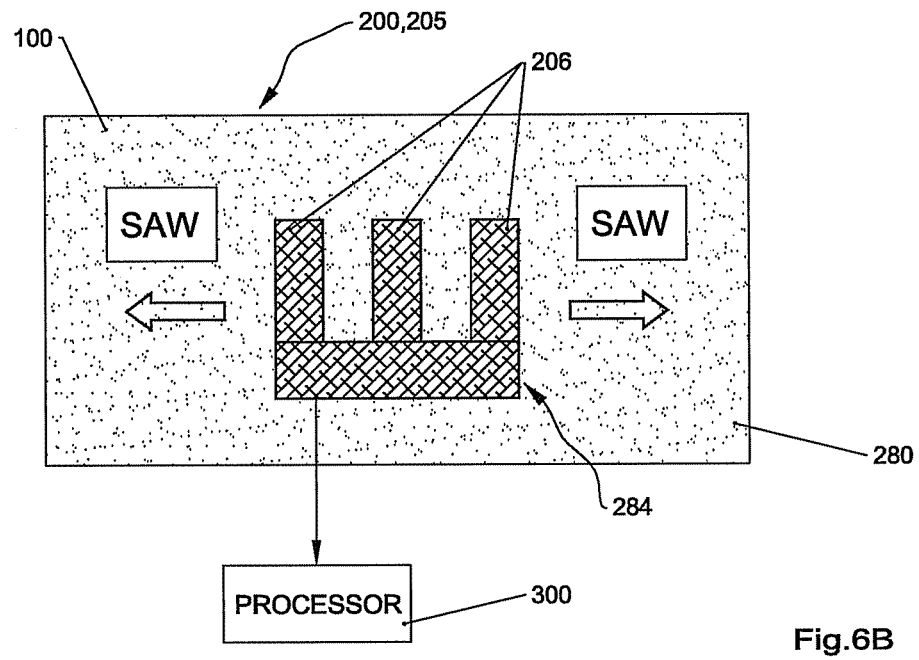
Figure 6C:
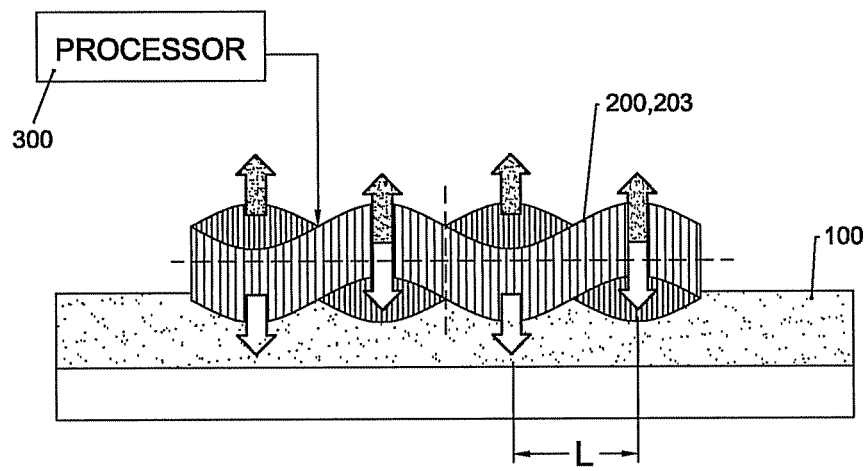

Reference is now made to FIGS. 6A-6C, which are illustrations of actuator 200, wherein actuator 200 is comprised of one or multiple piezo-elements 203. Actuator 200 may include a base portion 280 and an activating portion 282, wherein activating portion 282 is comprised of piezo-elements 203. It should be noted that electrodes must be included on piezo-elements 203. In many of the figures, these electrodes are not shown since they may be placed in any location, and the different possibilities for positioning of electrodes are known to those skilled in the art. In some embodiments, base portion 280 is also the activating portion 282 and is thus comprised of piezo-elements 203. As shown in FIG. 6A, actuator 200 is comprised of a base portion 280, wherein base portion 280 is a piezo-element 203, and thus acts as an activating portion 282. In some embodiments, multiple piezo-elements 203 are used. Actuator 200 may work in thickness and/or radial vibration modes thus generating SAW 121 on surfaces of skin 402. Vibrations of piezo-element 203 should occur in two planes, as depicted by arrows 202.

In the embodiment shown in FIG. 6B, actuator 200 is an integrated piezo-transducer, also known as an interdigital transducer (IDT) 205, having multiple elongated portions 206 or fingers, generating SAW on surfaces of skin 402 when the distance L between two of elongated portions 206 is proportional to one-half the length of the SAW.

The IDT 205 comprises a base portion 280 which also may act as activating portion 282. Activating portion 282 includes a piezoelectric material with an electrode portion 284 sprayed thereon in a particular configuration such as the one shown in FIG. 6B. It should be noted that the configuration shown in FIG. 6B represents three different possible setups for IDT 205. In one embodiment, base portion 280 is comprised of a piezoelectric material and acts as activating portion 282, with electrode portion 284 sprayed thereon in a "W" configuration as shown or in any known configuration for IDT. In another embodiment, base portion 280 is comprised of a material which is not piezoelectric, and activating portion 282 and electrode portion 284 are both configured in a "W" configuration as shown or in any known configuration for IDT. That is, the shape of the piezoelectric material matches the shape of the electrode. In a third embodiment, activating portion 282 and electrode portion 284 are both configured in a "W" configuration as shown or in any known configuration for IDT and are placed directly on skin 402. Thus, base portion 280 is activating portion 282, both of which have a particular configuration which is the same as electrode portion 284 and is suitable for use as an IDT. Electrode portion 284 faces away from skin 402, and base portion 280 and/or activating portion 282 is coupled to skin 402—either directly or with the use of a matching layer. In all of the above described configurations, electrode portion 284 is in electrical communication with processor 300. When a voltage is applied to electrode portion 284 via processor 300, then a thickness vibration is initiated in activating portion 282 and Lamb waves are initiated by a resonance effect. The energy distribution from the vibrating elements is in two opposite directions. The distance between elongated elements L is equal to half the wavelength of SAW which is excited with this method. Most electrode configurations concentrate the created energy in the surface layer up to 100μ. The number of electrode elements 206 can vary depending on the desired amplitude of the SAW. The IDT transducer elongated elements may be excited with magnetic or laser means, too.

Many other configurations for electrode portion 284 are possible, and are known in the art. For example, two electrode portions may be positioned facing each other such that elongated portions of one interlock with elongated portions of the other, with gaps therebetween. The electrical voltage is applied to both electrode portions and the direction of SAW propagation is in two directions. In some embodiments, a continuous electrode may be used. The distance between the elongated portions is equal to $\lambda_a$, i.e. the wave transits the distance between each pair of electrode elements precisely by the time equal to the phase of the exciting signal. Therefore the SAW intensity is proportional to the number of pairs of electrode elements. In another embodiment, electrode portion 284 includes two external active electrodes and multiple passive electrodes positioned between the active electrodes. By varying the number of passive electrodes it is possible to change the width of the range of frequencies to change resistance of radiation $N^2/4$ times, where N is the number of passive electrodes.

Reference is now made to FIG. 6C, which is an illustration of an actuator 200 such as the actuator shown in FIG. 6A, during vibrations. Actuator 200, after activation by processor 300, begins to vibrate in two directions—up and down—as shown by gray and white arrows, respectively. Vibrations of piezo-element 203 generate SAW on external surface 10 of skin 402 when a distance L between two maximal amplitudes of bending vibration modes are proportional to one-half the length L of the SAW. In this embodiment, piezo-element 204 is configured to work with symmetrical Lamb vibration modes. This method works similar to the IDT 205. The standing wave maximal amplitudes created in a thin plate are similar to elongated portions 206 of IDT 205, creating elastic deformations in the surface of skin 402 and exciting SAW thereon. In some embodiments, a coupler may be positioned between actuator 200 and skin 402. For example, a glue layer for attaching actuator 200 to skin 402 may be used, wherein the glue layer has a smaller acoustic velocity than piezo-element 203 but a larger acoustic velocity than skin 402.

Recent scientific works have shown that electric current applied to the liquids surrounding the biofilm may increase the efficacy of the antibiotics in biofilm dislodging—a phenomenon known as the bioelectric effect. Continuous direct electric current (DC) applied to the liquids surrounding the biofilm increase the efficacy of the antibiotic. This phenomenon is known as (DC) bioelectric effect; when radio frequency (RFC) alternating electric current (AC) is applied, analogous results may be achieved, and the process is known as radio frequency bioelectric effect. Thus, SAW excited simultaneously with continuous direct electric current (DC) or radio frequency (RFC) alternating electric current (AC) and transmitted to the liquids surrounding the biofilm should dramatically increase the efficacy of the antibiotics. This phenomenon may be effectively used in wound healing.

Figure 7A:
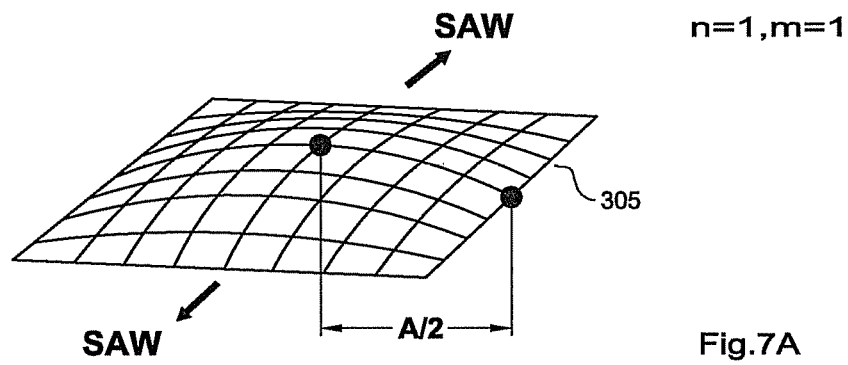
FIGS. 7A-7C are illustrations of piezo-electric plates which are vibrating in natural vibration modes.
Figure 7B:
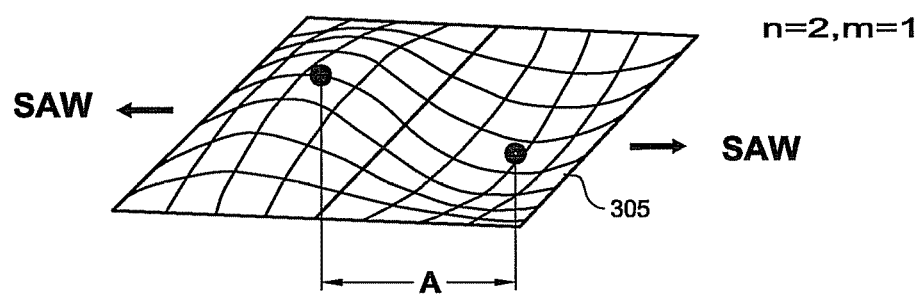
Figure 7C:
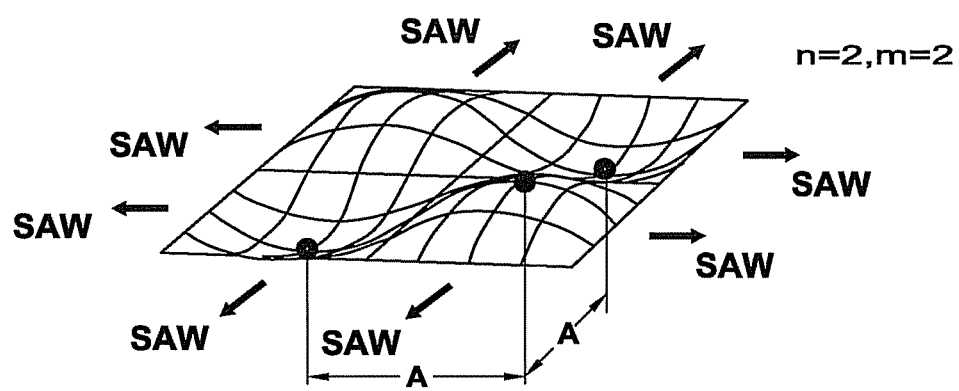

Reference is now made to FIGS. 7A-7C, which are illustrations of piezo-electric plates 305 which are vibrating in natural vibration modes. Piezo-electric plates 305 may act as actuators 200 in accordance with embodiments of the present invention. The vibrations excited in piezo-electric plates 305 may have different n and m, depending on the excitement frequency. A distance A between maximum amplitudes corresponds to one-half the wavelength of SAW activated by piezo-electric plate 305. This feature enable creation of SAW with varying characteristics such as wavelength and depth. Depth is generally equal to 1-2 wavelengths. By varying the n and m parameters, it is possible to cause micro-streaming, depth penetration of liquids, homogenization of cream particles, and other effects.

Figure 8A:
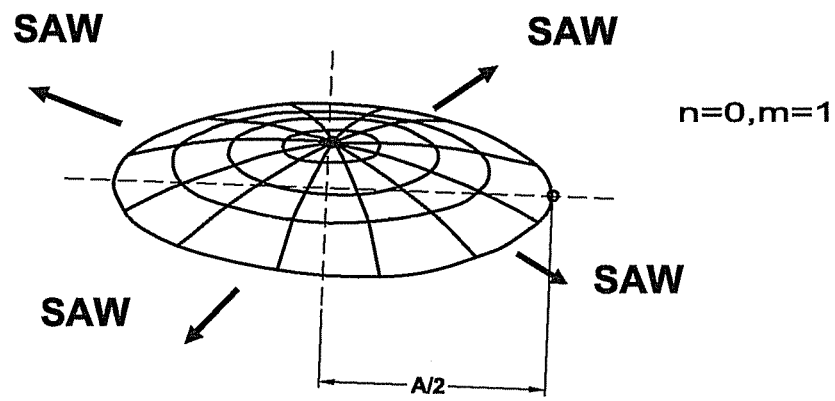
FIGS. 8A-8C are illustrations of piezoelectric disks which are vibrating in symmetric or antisymmetric Lamb vibration modes or in natural vibration modes.
Figure 8B:
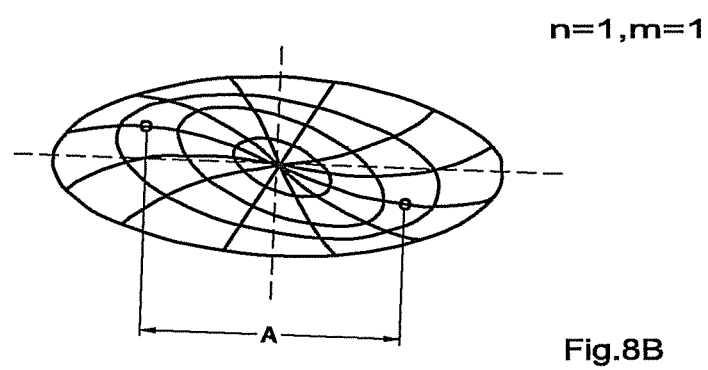
Figure 8C:
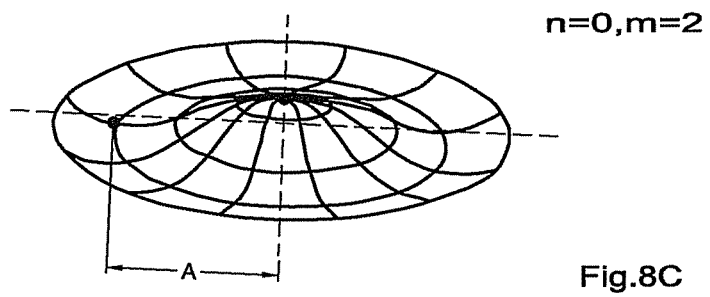

Reference is now made to FIGS. 8A-8C, which are illustrations of piezoelectric disks 306 which are vibrating in symmetric or antisymmetric Lamb vibration modes, or in natural vibration modes. The same dependence of n and m corresponds to excitement frequency, as described above with reference to FIGS. 7A-7C. Thus, SAW of varying different characteristics may be created because the distance A, between maximum amplitudes of excitement vibration corresponds to one-half the wavelength of SAW excited on the skin. It should be readily apparent that actuator 200 may have many other configurations, including ring, string, shell-like, strips, etc.

Figure 9A:
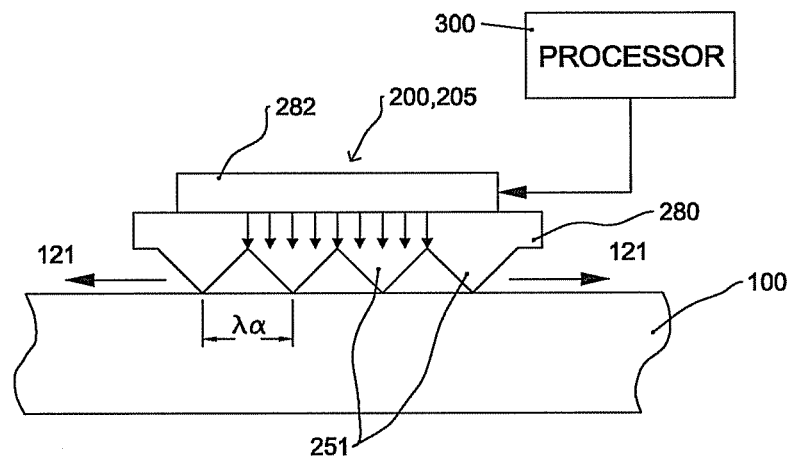
FIGS. 9A-9C are schematic illustrations of an actuator in place in accordance with several embodiments of the present invention.
Figure 9B:
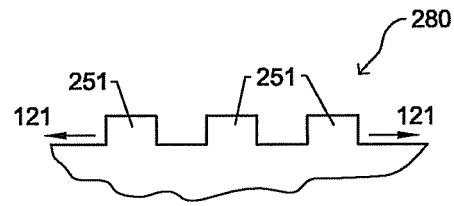
Figure 9C:
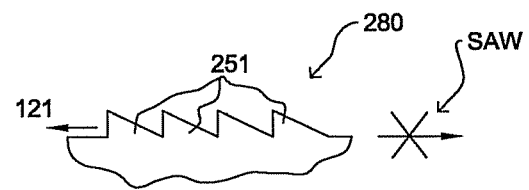

Reference is now made to FIGS. 9A-9C, which are schematic illustrations of actuator 200 in place in accordance with several embodiments of the present invention. The actuators 200 depicted in FIGS. 9A-9C may differ from each other in a mode of spatially-non-uniform and variable elastic deformations, and in an aspect of energy parameters emitted to the skin which is used for therapeutics needs. As shown in FIGS. 9A-9C, actuator 200 may have a "wedge" or "comb" type of configuration, wherein spherical waves (longitudinal and transverse) are transformed into surface waves.

As shown in FIG. 9A, actuator 200 includes a base portion 280 and an activating portion 282. Base portion 280 comprises protruding elements 251 which are in contact with skin 402. In the embodiment shown in FIG. 9A, each of protruding elements 251 has a triangular equilateral shape, and several of these protruding elements 251 are arranged in a row. Voltage is applied to activating portion 282 of actuator 200 via processor 300, which may include, for example, a power supply. Voltage from processor 300 excites elastic volumetric (three dimensional) vibrations in activating portion 282, which are transmitted to base portion 280 and to protruding elements 251. This results in production of SAW 121 in two opposite directions along skin 402. It should be readily apparent that in some embodiments, base portion 280 is comprised of piezoelectric material and in other embodiments, only activating portion 282 is comprised of piezoelectric material. In some embodiments, when base portion 280 is comprised of piezoelectric material, base portion 280 acts as activating portion 282.

Reference is now made to FIG. 9B, which is an illustration of base portion 280 having protruding portions 251 which are rectangularly shaped. This configuration causes a two-directional vibration along one axis. The requirement of acoustic synchronization is ensured by means of distances between the grooves, which are equal to $\lambda_a$. Thus the SAW which spreads along the grooves excites a surface wave in skin 402. Modification of the groove slope angle increases or decreases the vibration amplitude. As shown in FIG. 9C, protruding portions 251 may have an angled configuration such as a "comb" shape as well, enabling SAW propagation in one direction only.

Figure 10:
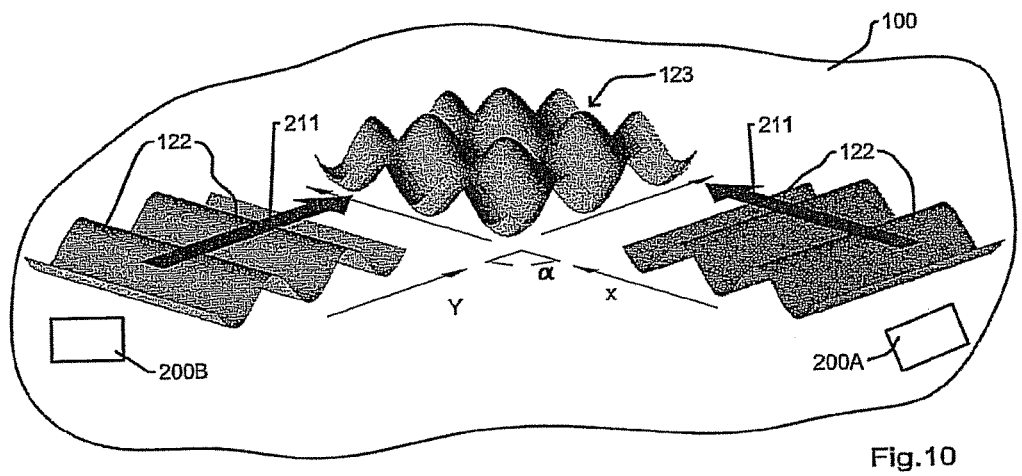
FIG. 10 is an illustration of one method for achieving SAW, showing a summation of SAW from two actuators placed at an angle relative to one another on a surface of skin.

Reference is now made to FIG. 10, which is an illustration of one method for achieving SAW, showing a summation of SAW from two actuators 200A and 200B placed at an angle α relative to one another on a surface of skin 402. Thus, running type waves 122 excited and transmitted by each of actuators 200A and 200B (in directions indicated by arrows 211) interfere with each other, thus forming standing waves 123 on the surface of skin 402. The waves' interferences in the areas of overlap concentrate acoustic energy. Thus, it is possible to create a concentrated SAW effect by strategic placement of actuators. In some embodiments, actuators 200A and 200B are connected to one processor 300. In other embodiments, separate processors may be used for each of actuators 200A and 200B.

Figure 11A:
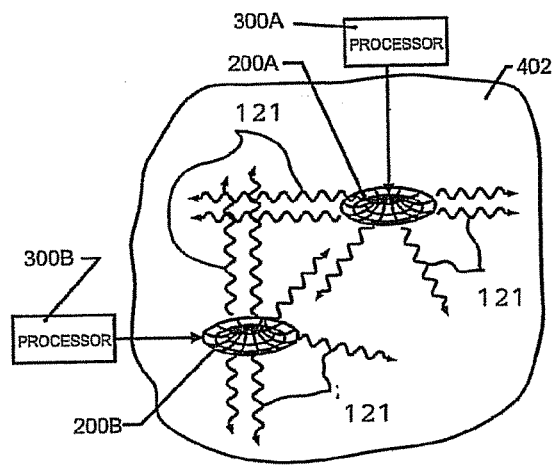
FIG. 11A is an illustration showing two actuators attached to separate processors.
Figure 11B:
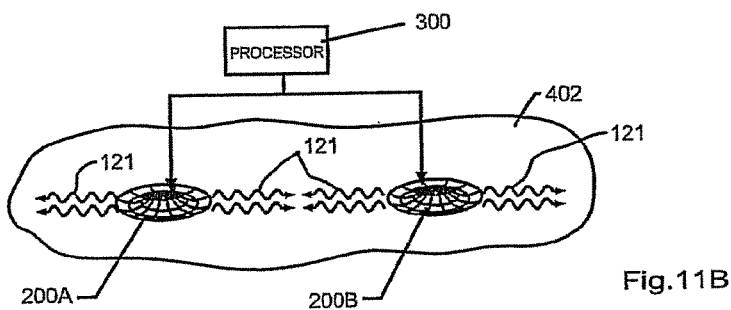
FIG. 11B is an illustration showing two actuators attached to one processor.

Reference is now made to FIGS. 11A and 11B, which are illustrations showing actuators 200A and 200B attached to separate processors 300A and 300B, and to one processor 300, respectively. As shown in FIG. 11A, a first actuator 200A is in electrical communication with a first processor 300A, and a second actuator 200B is in electrical communication with a second processor 300B. First and second actuators 200A and 200B are placed in different locations on skin 402, and may optionally be repositioned if necessary. In some embodiments, actuators 200A and 200B are at angles to one another. As shown in FIG. 11B, first and second actuators 200A and 200B may in some embodiments be in electrical communication with a single processor 300. The relative placement of actuators 200A and 200B remains relatively constant, but the overall positioning may be changed if necessary.

Figure 12:
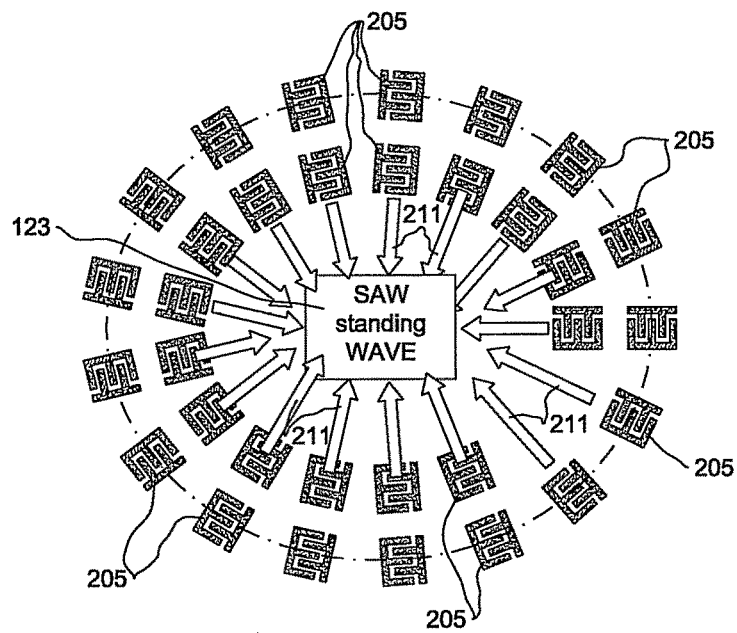
FIG. 12 is an illustration of another embodiment of the present invention, wherein SAW focused standing waves are created with serial IDT actuators placed in a circular configuration.

Reference is now made to FIG. 12, which is an illustration of another embodiment of the present invention, wherein SAW focused standing waves 123 are created with serial IDT 205 actuators placed in a circular configuration. This type of configuration may be useful for IDT 205 actuators, since IDT 205 actuators tend to create weak SAW; thus, it may be advantageous to focus the energy concentration. By placing IDT 205 actuators in a circular configuration, running waves propagating in a direction shown by arrows 211 (to the center of the circular configuration) will interfere with each other in the center, thus creating an area of standing waves 123 with much higher acoustic power.

Figure 13:
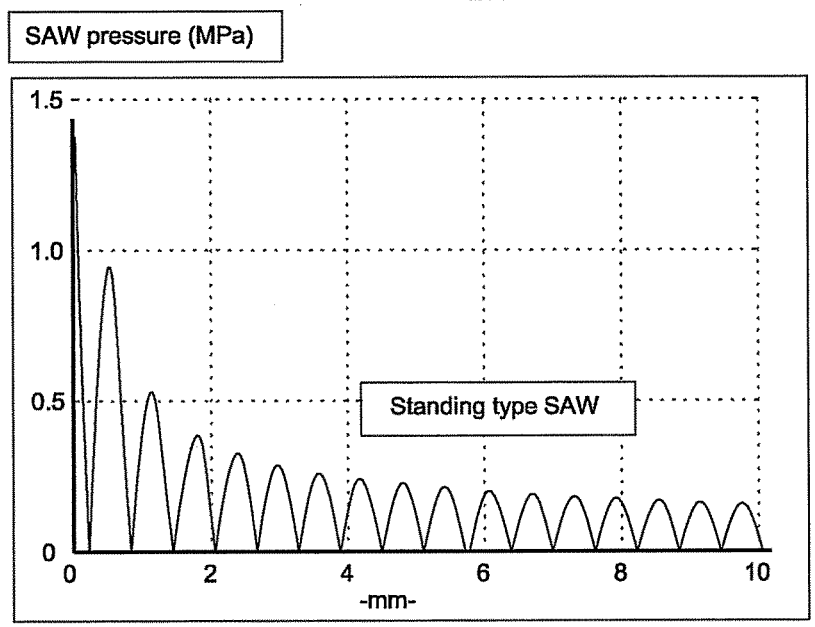
FIG. 13 is a graphical illustration of pressure from a focused standing wave versus distance from the center for high frequency acoustic waves obtained when actuators are placed circularly, as depicted in FIG. 12.

Reference is now made to FIG. 13, which is a graphical illustration of pressure from a focused standing wave versus distance from the center for high frequency acoustic waves obtained when actuators are placed circularly, as depicted in FIG. 12. The pressure greatly increases in the central zone due to the focusing effect.

A focused effect such as the one described above with respect to FIGS. 12 and 13 may also be obtained by using a ring-shaped piezo-element for activating portion 282 of actuator 200. Running waves are directed inwardly, towards a center of the ring-shaped piezo-element. Interaction of these running waves with one another causes formation of standing waves at the center. The minimal thickness of a ring-shaped piezo-element for this purpose may be in the order of 0.05 mm to 0.1 mm. The inner radius of the ring-shaped piezo-element may be in the order of 1-100 mm. Other dimensions are possible as well. In some embodiments, the ring-shaped piezo-element has an outer layer, which may be, for example, an absorbing material such as rubber, silicone, polymer or metal or any other suitable absorbing material. The absorbing material may be adapted to absorb the acoustic vibrations which are directed outwardly from the ring, if it is desired. As in all of the actuators of the present invention, a power supply system may be adapted to supply electric input to the ring-shaped piezo-element. The frequency of the electric input may be selectively controlled. Electric input from the power supply may be delivered to the conductive material of ring-shaped piezo-element, which may then cause substantial vibrations of the ring-shaped piezo-element. For example, the electric input delivered to the ring-shaped piezo-element may cause thickness, longitudinal, or torsion or any other acoustic wave form. The selected frequency may be dependent upon various system parameters, including, but not limited to the thickness of the piezoceramic material used for ring-shaped piezo-element. For example, the frequency applied to a ring-shaped piezo-element having a thickness of 0.05 mm may be approximately 20 MHz and the frequency applied to a ring-shaped piezo-element 220 having a thickness of 50 mm may be approximately 0.1 MHz. Other frequencies and thicknesses may be selected. In some embodiments, the ring-shaped piezo-element is constructed of several arc sections, which may be excited simultaneously or sequentially, or in any other combination, resulting in lower energy assumptions with higher focused results. In some embodiments, serially positioned ring-shaped piezo-elements may create multiple areas of focused SAW effects.

Figure 14A:
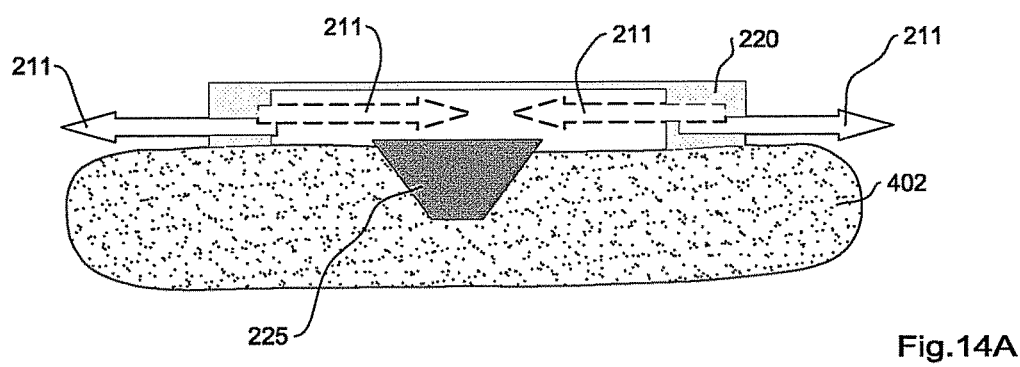
FIG. 14A is an illustration of an embodiment of the present invention, showing creation of SAW focused standing waves using a ring-shaped piezo-element.

Reference is now made to FIG. 14A, which is an illustration of an embodiment of the present invention, showing creation of SAW focused standing waves using a ring-shaped piezo-element 220, as shown in FIG. 14B. Ring-shaped piezo-element 220 is placed on skin 402. When stimulated, SAW form outwardly and inwardly with respect to ring-shaped piezo-element 220, as depicted by arrows 211. This causes a focusing of running waves at a center area resulting in standing SAW in a focused area 225 as depicted in FIGS. 14A and 14B, and may create extremely high pressure or temperature at focused area 225.

Additional embodiments of actuators which may be used in the present application are disclosed in U.S. Patent Publication No. 2005/0268921; U.S. Patent Publication No.

2005/0095351; and U.S. Patent Publication No. 2005/0038376, all of which are incorporated by reference herein in their entireties.

2. Enhanced Disinfection Employing SAW Actuators in Disinfection Procedure

Skin disinfection has been the subject of research for many years. In hospital practice removal of bacteria is essential for preoperative preparations and for intravascular catheterization of any kind. The disinfection in those cases is vital in order to prevent septicemia and even death. At operation sites and for intravascular catheterization, biofilms should be removed from the deeper layers of the skin as well as from the surface so that when the knife, blade, needle or any foreign body of indwelling medical device reaches the blood or deeper tissues it will be free from pathogenic bacteria.

Disinfection is not always satisfactory due to skin structure—irregularity of the skin which contains hydrophobic pockets, air bubbles, fissures and crevices which compromise sufficient penetration, and due to quick drying of the disinfectant. It is known in the art that ultrasound is an enhancer of antibiotic action, both by enhancing the bactericidal effect of antibiotics and significantly increasing the transport of the antibiotic across biofilms.

Reference is now made to FIG. 15, which is a schematic illustration of an acoustic pad 500 placed on skin 405, in accordance with embodiments of the present invention. Acoustic pad 500 may be, for example, a disinfecting patch having the ability to achieve more efficient disinfection before surgical procedures, catheterization and venipuncture. Acoustic pad 500 includes an actuator 200 and a processor 300 either separate from or attached to actuator 200. In some embodiments, acoustic pad 500 is a disposable patch, and may have multiple layers, including, for example: a transparent protective layer, a permeable adhesive layer, a disinfecting agent layer, a layer with PZT actuator, and a protecting cover. Prior to insertion of a medical device into the body, the protective layer is removed from acoustic pad 500, and adhesive layer is placed against the skin 402 at the insertion site of skin 402. Acoustic pad 500 is configured to enhance the disinfecting ability of a disinfectant which is contained in the disinfecting layer, such as, for example, chlorohexidine or povidine. Acoustic pad 500 may be any suitable size, such as but not limited to, about 10 cm×10 cm for certain applications.

Actuator 200 causes SAW of Rayleigh, "pseudo" Rayleigh or Lamb type, matched as 121 to be created on the skin. SAW 121 can mechanically enhance the penetration and distribution of disinfectants evenly and thoroughly, and acoustic pad 500 maintains a moist environment for bacteria to enter the intravenous catheter insertion site. Acoustic pad 500 is reversibly attached to the skin 402, and may remain on the skin 402 for at least a week, although disinfectation may take place in as little as 2 to 5 minutes.

In another embodiment, acoustic pad 500 is pre-cut, and may be positioned on skin 402 after skin 402 is already in place, thus protecting the already formed insertion wound from bacteria contamination.

According to methods of the present invention, acoustic pad 500 may be used to enhance the preparation of the skin for venipuncture or catheter insertion sites prior to catheterization and for post insertion hygiene maintenance; disinfection of lacerated wounds, necrotic wounds and burns; and wound healing. In addition to disinfecting action prior to catheter insertion (or other devices), acoustic pad 500 may be used as a hydrophilic wound dressing to absorb exudates and cover the wound caused by the use of vascular and other medical devices (IV catheters, CVL, arterial catheters, dialysis catheters drains, externally placed orthopedic pins). It is also intended to reduce local infections, catheter related blood stream infections, and skin colonization of microorganisms.

The energy levels may be controlled by medical professionals. Activation of SAW by actuator 200 causes micro streaming of an active agent placed on the wound, resulting in better distribution of the agent on the surface. In some embodiments, multiple actuators 200 may be used. If two actuators are applied at the angle to each other, running waves in each direction will result in standing waves in the cross region. These standing waves induce disinfectant penetration into the skin's deeper layers.

In some embodiments, SAW actuators 200 may be used in combination with existing, commonly used patches such as, for example, Biopatch™. The use of a patch such as acoustic pad 500 may reduce the necessity to replace peripheral catheters every two days, as is the current practice.

Reference is now made to FIGS. 16A and 16B, which are illustrations of an acoustic glove 502 in accordance with embodiments of the present invention. Acoustic glove 502 may have an outer layer and an inner layer, and may be comprised of gauze, cotton, wool, polyester, rayon or any other natural or synthetic material on the outer layer, and latex or any other non-latex plastic or polymer on the inner layer. The outer layer of acoustic glove 502 is pre-treated with a disinfectant such as dacron, chlorhexidine gluconate, alcohol, iodine or any similar disinfectant or any combination thereof. A packaging shield protects the disinfecting liquid from vaporizing. The packaging shield may be opened at the time of the disinfecting procedure. Acoustic glove 502 may include a sleeve portion of any suitable length for placing on an arm, or may not have a sleeve portion at all. Upon activation of SAW via actuators 200, acoustic glove 502 is effective against bacteria, virus and picons, as well against vancomycin resistant enterococci (VRE) and methacillin resistant staphylococci aurieus. Acoustic glove 502 can enhance a pre-operative disinfecting procedure.

In some embodiments, finger portions 504 are partially or completely comprised of latex, and a central portion is comprised of gauze, cloth, cotton, wool, polyester, rayon or any other natural or synthetic material. Thus, the central portion may be pre-treated with chlorhexidene gluconate, alcohol, iodine or any similar disinfectant.

In some embodiments, as shown in FIG. 16B, portions of acoustic glove 502 are fitted with actuators 200, which are connected to a processor 300. In this embodiment, processor 300 is a battery-powered system. Portions which have actuators 200 thereon may include, for example, latex portions of acoustic glove 502, and may be confined to finger portions 504 or may be placed on a central portion of acoustic glove 502. Mechanical vibrations activated by actuators 200 enable deeper penetration of the disinfecting liquid to the skin layers, providing better results.

3. Wound Healing, Wound Dressing, Surgical Adhesion Prevention

Wound healing undergoes several phases, which are known to be affected by ultrasound. The first phase is the inflammatory phase, wherein ultrasound causes a degranulation of mast cells resulting in the release of histamine. Histamine and other chemical mediators released from the mast cells are thought to play a role in attracting neutrophils and monocytes to the injured site. These and other events appear to accelerate the acute inflammatory phase and promote healing. The second phase is the proliferative phase. Ultrasound has been noted to affect fibroblasts and stimulate them to secrete collagen. This can accelerate the process of wound contraction and increase tensile strength of the healing tissue. Connective tissue will elongate better if both heat and stretch are combined. Continuous ultrasound at higher therapeutic intensities provides an effective means of heating of deeper tissue prior to stretch.

Several beneficial effects have been reported from contact ultrasound physiotherapy: local improvement of the blood circulation, heating of the tissue, accelerated enzyme activity, muscle relaxation, pain reduction, and enhancement of natural healing processes.

Despite these beneficial effects, current techniques of medical physiotherapy using ultrasonic waves are limited by the necessity of providing a direct contact interface between the ultrasonic transducer and the tissue to maintain an effective transmission of the ultrasonic waves from the transducer to the tissue. This requirement makes ultrasound treatments unsuitable for many applications including, for example, treatment of fresh or open wounds resulting from trauma, burns and surgical interventions.

Figure 17:
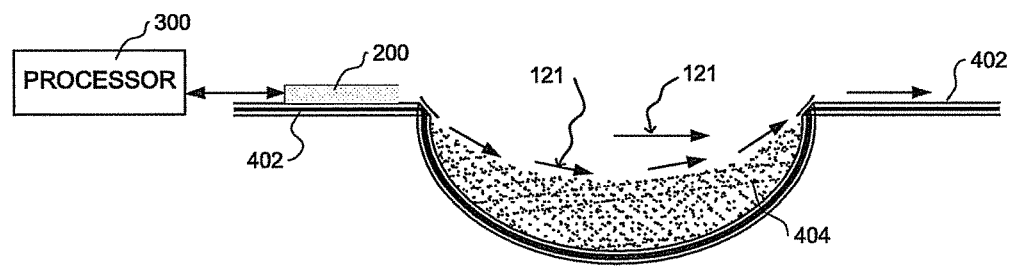
FIG. 17 is a schematic illustration of the use of an actuator for SAW propagation on the surface of a wound, wherein the actuator is placed nearby at the site of healthy skin.
Figure 18:
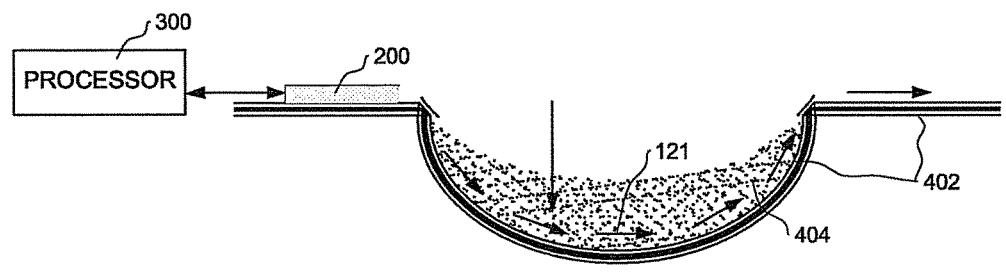
FIG. 18 is an illustration of distribution of SAW between an inner surface of the wound and the skin.

Reference is now made to FIG. 17, which is a schematic illustration of the use of an actuator 200 for SAW propagation on the surface of a wound 404, wherein actuator 200 is placed nearby at the site of healthy skin 402. Since SAW have an ability to travel between two media, they may be distributed at a wound surface without direct contact. Reference is now made to FIG. 18, which is an illustration of distribution of SAW between an inner surface of wound 404 and skin 402. Frequencies may be in a range of 0.1 Hz-10 MHz.

In some embodiments, SAW may be distributed in both areas either simultaneously or non-simultaneously. Moreover, in some embodiments, wound 404 is treated with an active pharmaceutical agent (drug, gel, etc). SAW may be distributed between the active pharmaceutical agent and air, between the active pharmaceutical agent and the wound, and between the wound and the underlying skin. Any and all of these combinations are possible. In yet additional embodiments, SAW may be created on the skin surrounding the wound. SAW actuator creates simultaneous wave distribution on the wound surface and in along external/internal wound perimeter. All of the methods disclosed herein may be applied to external or internal wounds.

Figure 19:
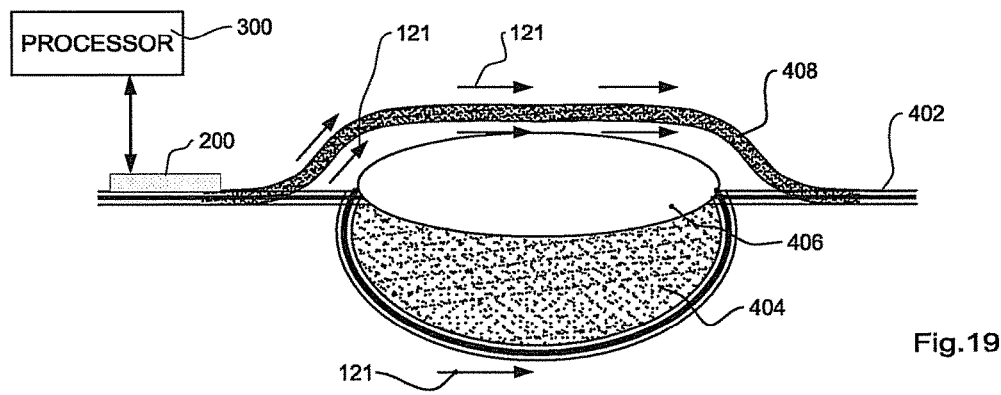
FIG. 19 is an illustration of an actuator for producing SAW in combination with a wound dressing.

Reference is now made to FIG. 19, which is an illustration of an actuator 200 for producing SAW in combination with a wound dressing 408. Wound dressing 408 is placed over pharmaceutical agent 406. SAW are produced at the interface between wound dressing 408 and pharmaceutical agent 406. Frequencies may be in a range of 1 KHz-20 MHz.

Figure 20:
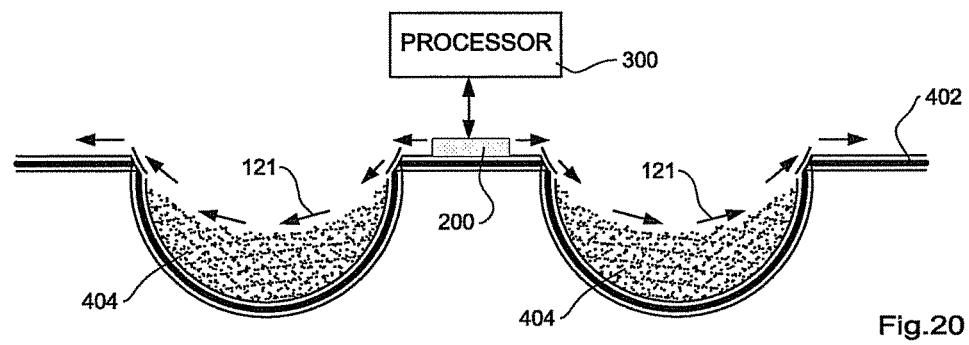
FIG. 20 is an illustration of SAW activation for treatment of multiple wounds.

Reference is now made to FIG. 20, which is an illustration of SAW activation for treatment of multiple wounds 404. As shown in FIG. 20, two or more wounds 404 may be treated simultaneously or sequentially using one actuator 200. Actuator 200 is placed on a portion of healthy skin 402 which lies between two wounds 404. Actuator 200 is configured to propagate SAW in multiple directions, allowing treatment of both wounds 404 which are on opposite sides of actuator 200. This spreading of waves in multiple directions occurs automatically with the use of actuator 200.

Figure 21:
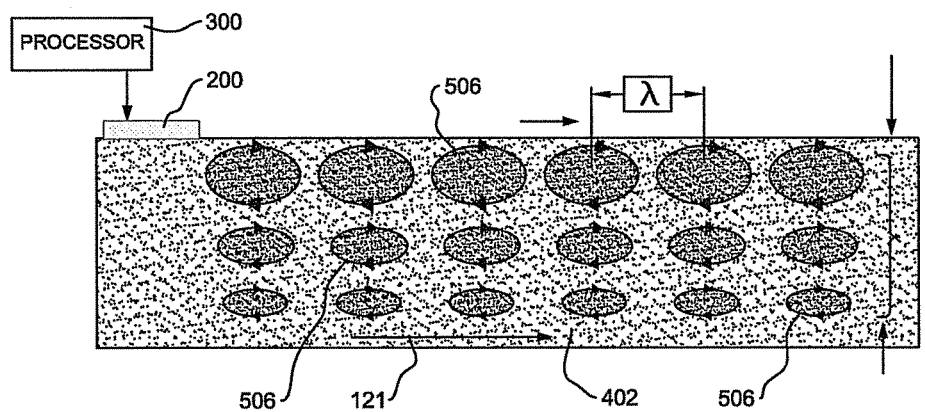
FIG. 21 is a schematic illustration of SAW activity, including depth, intensity and direction.

Reference is now made to FIG. 21, which is a schematic illustration of SAW activity, including depth, intensity and direction. As the surface acoustic waves penetrate to the depths up to two wave lengths, the penetration depths may be controlled through wave length, which depends on frequency. As shown in FIG. 21, when SAW has a relatively long wavelength, deep penetration is achieved, in comparison to SAW with short wavelengths. Particles vibrate elliptically, as indicated by ellipses 506, and the energy intensity decreases with increased distance from the surface. This is depicted schematically in FIG. 21 by showing increasingly smaller ellipses as the distance from the skin 402 surface increases. The intensity is controlled by the voltage applied by processor 300, and the wavelength is controlled by the frequency applied. SAW actuators 200 may work in a range of between 10 Hz-10 MHz in continuous and pulse regimes. These features enable management of the depth of SAW distribution in a discrete or continuous manner, depending on the requirements. When SAW are activated with a short wavelength by stimulating with low frequencies, a thin layer of depth penetration is achieved.

Figure 22:
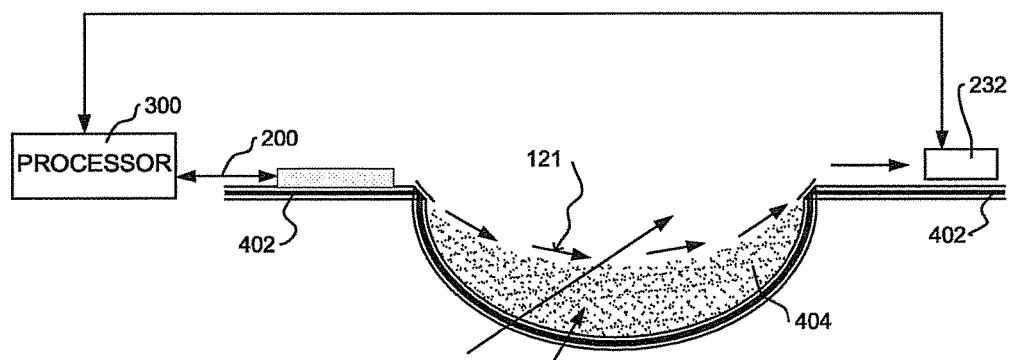
FIG. 22 is a schematic illustration of wound healing using an actuator 200 and a sensor 232.
Figure 23:
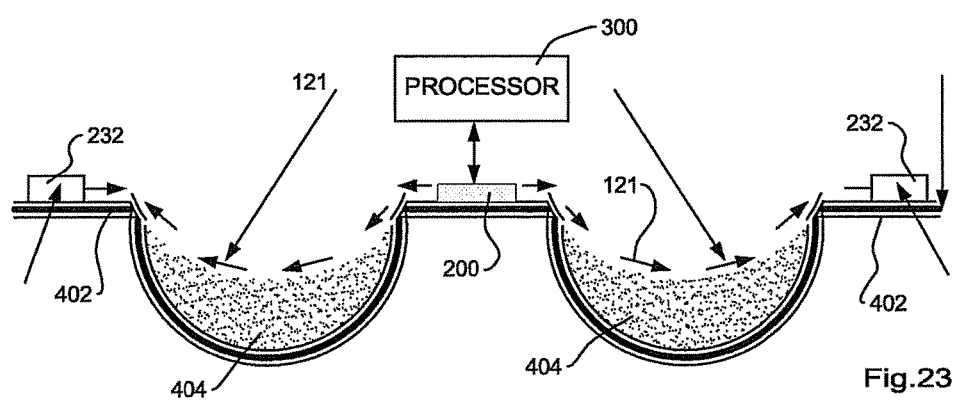
FIG. 23 is a schematic illustration treatment and sensing of multiple wounds with an actuator positioned between two wounds and sensors on opposite sides of the wounds.

Reference is now made to FIG. 22 which is a schematic illustration of wound healing using an actuator 200 and a sensor 232. In the embodiment shown herein, actuator 200 is placed on healthy skin 402 on one side of wound 404, and sensor 232 is placed on healthy skin 402 on an opposite side of wound 404. Both actuator 200 and sensor 232 are in electrical communication with processor 300. In some embodiments, acoustic sensor 232 is based on differences in acoustic wave velocity in healthy versus wounded skin and may include a miniature photo device and may include web-based and telemedicine means. Processor 300 may control the amount of SAW in real-time by comparing the measured parameters with desired parameters, thus creating a feedback loop. Similarly, as shown in FIG. 23, treatment and sensing of multiple wounds is possible, by, for example, placing actuator 200 between wounds 404 and sensors 232 on opposite sides of wounds 404. Both sensors 232 and actuator 200 are in electrical communication with processor 300 and may optionally provide a continuous feedback system, as described above with reference to FIG. 22.

The principle of the sensor action is based on different surface acoustic wave SAW velocities in the wound structure, healthy skin and healing wound. The sensor achieves an electrical signal in response to SAW direct piezoelectric effect, and thus can measure wave propagation velocity, which differs in healthy versus wounded skin. In some embodiments, it is possible to estimate the efficiency of wound treatment by measuring the velocities of SAW transmission using an acoustic skin analyzer. It has been found that during the first phase of wound healing, SAW have velocities of 50-90 m/s, in the second phase the velocities decrease to 35-49 m/s and during the third phase, velocities decrease yet further to 25-35 m/s. SAW velocities in healthy skin were found to be 18-25 m/s. These measurements correlate with cytological and histological findings.

In some embodiments, multiple actuators may be used in combination to treat one area. Thus, for example, a first actuator may be placed in the nearby region (approximately 0.5-2 cm distance from the wound) and a second actuator may be placed in a more distant region (approximately 2 m). The first actuator acts in a "Fresuel" regime, wherein a more focused beam is achieved, and the second actuator acts in a "Fraunhofer" regime, wherein a beam of an extended area is achieved. An interaction between the waves of the first and second actuators results in a standing wave at the cross area of the two beams.

Figure 24:
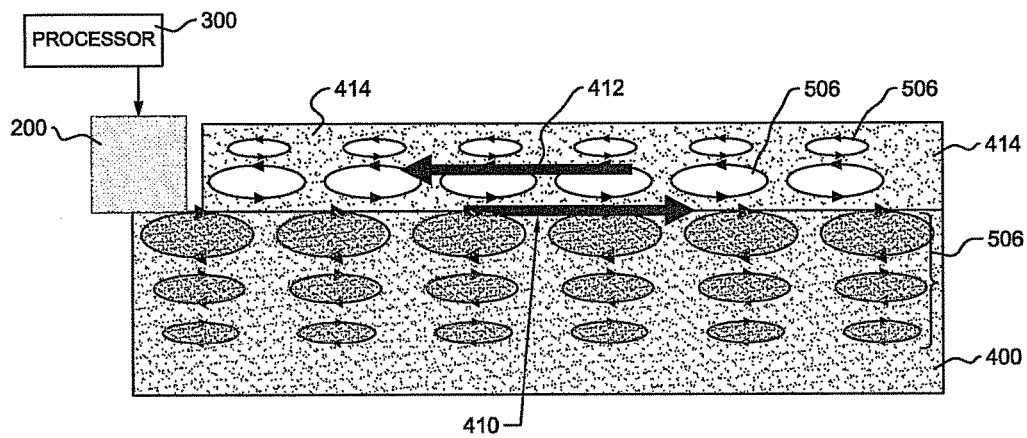
FIG. 24 is a schematic illustration showing opposite directions of SAW propagation and liquid microstreaming.

Reference is now made to FIGS. 24-28, which are schematic illustrations of a method of micro-streaming using SAW, in accordance with embodiments of the present invention. A micro-streaming effect is created due to the running waves achieved in the SAW process and elliptical oscillations of the surface particles. The result of these two characteristics is liquid micro-streaming, wherein a direction of micro-streaming is opposite to the direction of SAW propagation, because the elliptical motion of surface particles causes the contacting liquid particles to move in an opposite direction. Reference is now made to FIG. 24, which is a schematic illustration showing opposite directions of SAW propagation and liquid microstreaming. A liquid 414 covers a body tissue 400. Actuator 200 and processor 300 are placed on a portion of the surface of body tissue 400. Upon activation, SAW are created in a SAW propagation direction, as shown by arrow 410. Due to the elliptical motion of particles, as shown schematically by ellipses 506, liquid 414 begins to move in an opposite direction, as shown by arrow 412. Micro-streaming may aid in wound healing. The velocity of the liquid during micro-streaming may be in a range of 1-50 microns/min, depending on the dynamic parameters of the liquid and the intensity of SAW.

Figure 25:
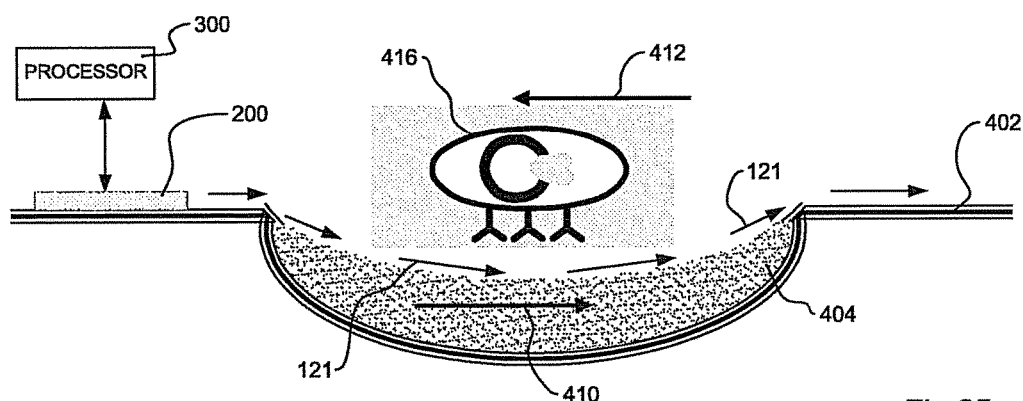
FIG. 25 is a schematic illustration showing the influence of SAW on bacteria due to micro-streaming.

Reference is now made to FIG. 25, which is a schematic illustration showing the influence of SAW on bacteria 416 due to micro-streaming. Micro-streaming will result in inhibition of bacteria from docking and adhering to the surface, and further results in streaming of bacteria within the liquid out of the wound site in a direction opposite to SAW propagation as shown by arrows 410 and 412. This process is similar to micro-pumping, but without the need for vacuum. Methods for micro-streaming may be applied with or without a wound dressing.

Figure 26:
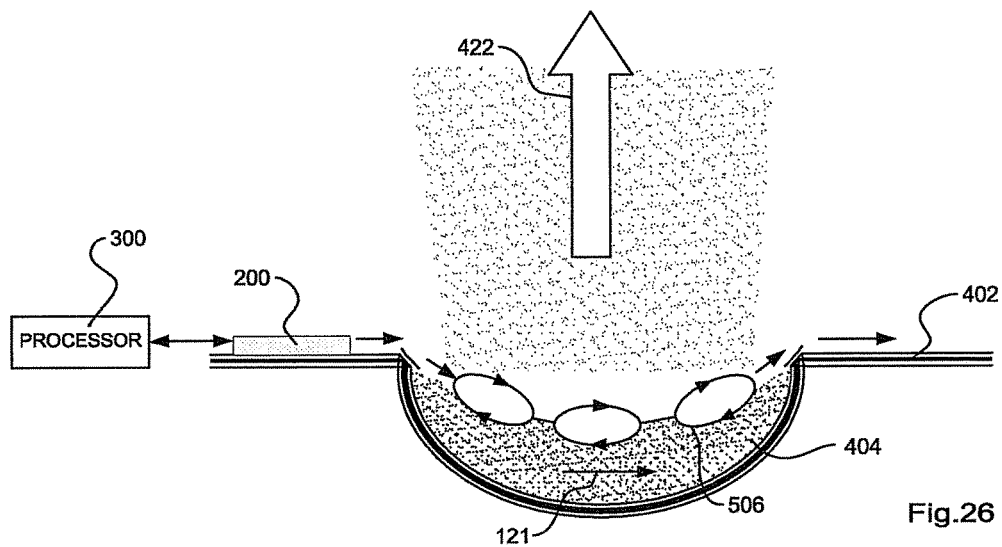
FIG. 26 is a schematic illustration showing the influence of SAW on drying, in accordance with additional embodiments of the present invention.

Reference is now made to FIG. 26, which is a schematic illustration showing the influence of SAW on drying, in accordance with additional embodiments of the present invention. SAW produce micro-vibrations in the liquid molecules, which thus obtain kinetic energy and vaporize more easily. Thus, SAW can enhance a drying effect, wherein vaporization occurs away from the wound site, as shown by arrow 422.

Figure 27:
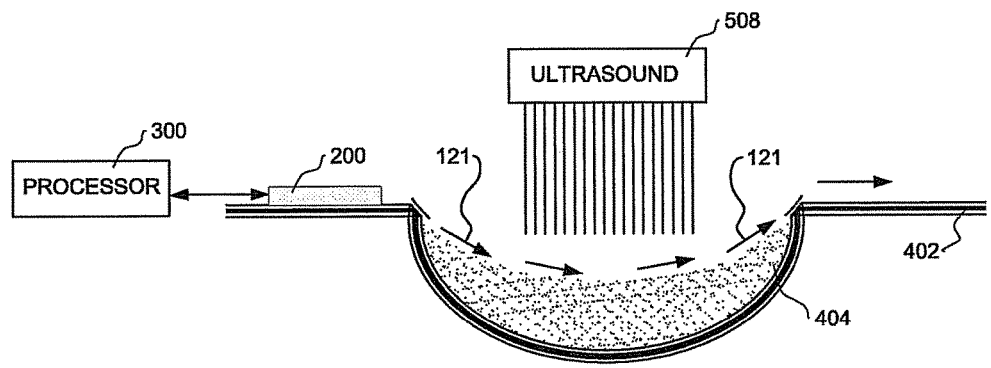
FIG. 27 is a schematic illustration showing SAW applied to wound healing, with the addition of a conventional ultrasound transducer.

Reference is now made to FIG. 27, which is a schematic illustration showing SAW applied to wound healing, with the addition of a conventional ultrasound transducer 508. When conventional ultrasonic waves of sufficient intensity (such as in a range of about 0.5-10 W/cm$^2$) are directed at an air-liquid interface, the liquid may work as a nebulizer to produce a very fine fog or mist. Aerosol mists produced by ultrasound are preferred as compared to drugs in a liquid or moisture state because a smaller particle size can be obtained. The application of two techniques together can enhance wound healing.

The methods described herein topically transmits acoustic energy to a medicine on the wound surface (such as antibiotics, for example) without the need to contact an infected, inflamed or painful tissue with an instrument. Second, a significant debridement, cleansing and bactericidal effect can occur when SAW of Rayleigh or "pseudo" Rayleigh or Lamb type reach and are distributed on a wound surface using the method of the present invention. Third, aside from the bactericidal effect and advantages of non-contact treatment, use of the methods of the present invention permits a significant reduction in volume of liquid medicines used as compared with traditional methods for wound treatment and allows for precise dosage of the acoustic energy, rate and duration as per physician decision. The methods of the present invention decrease healing times for inflammatory and purulent infected wounds, up to 1.5 to 2 times faster than traditional methods. This effect results from a bactericidal, blood flow increasing and mechanical cleansing effect of the activated drug particles, which obtain energy due to the acoustic waves. All of these advantages may be further enhanced by the use of conventional ultrasound.

Specific advantages of the combination of ultrasound and SAW include the following: energized and highly activated antibiotics, drug penetration into the tissue surface up to 0.5 mm in depth, more efficient destruction of the surface bacteria, etc. The SAW of the present method also stimulates healthy cell growth to aid in granulation and epitheliation of the healing tissue. The method of the present invention offers an approach that may re-establish use of some traditional antibiotics and establish a method for fighting bacteria without antibiotics.

The effect of the method of the present invention in highly activating antibiotics may allow some traditional antibiotics to overcome bacteria which have become resistant to that antibiotic. Moreover, independent of the sonication effect of the antibiotics, the low frequency SAW applied in the method of the present invention physically inhibit biofilm formation. The combination of the highly activated antibiotics and of the SAW in the method of the present invention produce a strong bactericidal effect not found in regular topically applied or orally ingested antibiotics. This combined effect may significantly increase the healing of purulent infected wounds.

In some embodiments, the SAW and/or combined SAW/conventional ultrasound may be further enhanced by the addition of a laser beam. In some embodiments, the conventional ultrasound is continuous and in other embodiments the conventional ultrasound is pulsed. Moreover, the laser therapy may include a pulsed, scanned or gated laser continuous wave laser or incoherent radiation of ultraviolet therapy. The combination of SAW, conventional ultrasonic waves, laser beams and energized medicines (highly activated by ultrasonic waves and laser beams) should destroy the surface bacteria and result in a higher level of disinfection by the energized liquids as compared to ordinarily applied liquids. In addition, the SAW process and conventional ultrasound and laser energy also stimulates healthy cell growth to aid in granulation and epitheliation of healing tissue. Embodiments of the present invention relate to methods and systems for wound treatment using a SAW process combined with different energy sources, such as a laser, conventional ultrasound, electric current, magnetic field, ultraviolet, microwaves, radio frequency, light-emitting diodes (LEDs) and or equivalent sources, as will be apparent to one skilled in this art.

Butterfly Skin Bandage or Patch

Post-operative adhesions are a common surgical complication. Adhesions are particularly troublesome in a variety of locations, e.g., between the pericardium and sternum following open heart surgery, in the abdominal cavity following bowel procedures and, especially, in the retroperitoneal space involved with gynecological reconstruction. Two primary approaches have been explored. The first involves implantable barrier films prepared, for example, from hyaluronic acid or hydrogonic acid or oxidized cellulose, but this approach has not met with success because the location of where to place the film to prevent adhesions is not easily determined. The second approach involves the instillation of a bolus of solution, e.g., N,O-acetylchitosan, to wet the general area where adhesions might be expected. Although this approach seems promising, satisfactory products for this approach have not yet been developed. These adhesions usually form during the first post-operative week. Therefore, the task is to prevent fibroblasts (which produce the collagenous adhesions) from adhering to local tissue surfaces during the first week.

Currently available butterfly skin bandages function well, but fail rapidly as adhesion decreases with movement of skin and hydration at the bandage site. A non-adhesive butterfly bandage comprising small SAW actuators could be a solution to this need. Such devices can also optionally comprise drugs or the like to be released transdermally. Such devices may optionally be used with decabitous ulcers, in venostatis situations (in diabetic patients, pressure on the skin and bone causes erosion and ulcer). In addition, such a wound dressing device can be coupled with a moiety, such that the moiety can enhance wound healing (e.g., cell growth).

The anti-adhesion solutions of the current invention are expected to prevent cellular attachment. The anti-adhesion embodiments herein are optionally in various forms (e.g., liquid application forms, film application forms, etc.).

Dressings (hydroactive and conventional gauzes) for surgery can be used with the addition of SAW actuators for prevention of adhesion. Some embodiments can optionally be a mesh (e.g., synthetic, metal, fabric) coating with the addition of SAW actuators, wherein the combined coating is laid directly over the wound cavity. In some embodiments, bacteriostatic dressings and/or bactericidal dressings may be used. In other embodiments, silver and/or zinc and/or titanium oxides, which have bactericidal characteristics, may be used with SAW actuators to further increase their efficacy. SAW actuators may be incorporated into the dressings or may be placed at their peripheries.

Such embodiments would allow for flexible wound dressings which allow air penetration, minimize infection and adhesion, may be water repellant, and which are easy to apply and remove. These types of wound dressings allow patients to avoid infection and decrease the need for painful bandage changes.

Wound Treatment Employing Saw Induced Micro Pumping

The treatment of open wounds that are too large to spontaneously close is a troublesome area of medical practice. Closure of an open wound requires inward migration of surrounding epithelial and subcutaneous tissue. Some wounds, however, are too large and are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue. It is therefore desirable to provide a technique for increasing blood circulation within wounded tissue to promote spontaneous healing and to reduce infection.

Poor blood circulation and infection at the wound may also hinder attachment of skin grafts or flaps upon wounded tissue. Skin grafts and flaps will not attach to tissue that is poorly vascularized, infected or necrotic. However, grafts and flaps can be used with much greater success on tissue that, although wounded, is able to form granulation tissue. Accordingly, a technique for promoting blood circulation at the wounded tissue would also promote successful attachment, or "take," of skin grafts or flaps to the wounded tissue as a consequence of increased blood circulation within the grafts or flaps.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counter-productive. Additionally, the size or type of a particular wound may prevent the use of sutures to promote wound closure.

It would therefore be desirable to provide a method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It is therefore desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

A method of SAW-induced micro-pumping can promote tissue migration and facilitate closure of the wound. By creating the SAW induced micro pumping, a negative pressure is formed, which facilitates wound closure. This method may be applicable to wounds, burns, infected wounds, and live tissue attachments. A wound treatment method involves a fluid impermeable wound cover which is sealed over a wound site. A screen in the form of an open-cell foam screen or a rigid porous screen is placed beneath the wound cover over the wound. SAW micro pumping action supplies suction within the wound cover over the treatment site.

It must be emphasized that SAW propagation in the interface wound-dressing material results in non-sticking of the dressing material. The dressing material serves as an acoustic transmission line and acoustic energy is distributed—even to relatively distant locations. Thus, SAW can be used to prevent and treat pressure sores (in a bandage or patch configuration as well in a sock and partial sock configuration), for treatment of burns, for removal of wound dressings in a non-stick fashion and for diabetic wound preventing.

In accordance with the present invention a wound treatment method may be based on the same SAW distributing methods as described above and may provide wound treatment by applying micro pumping to the wound in a controlled manner for a selected time period. The application of micro pumping to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of micro pumping include infected open wounds, decubitus ulcers, dehisced incisions, partial thickness burns, and various lesions to which flaps or grafts have been attached.

Figure 28:
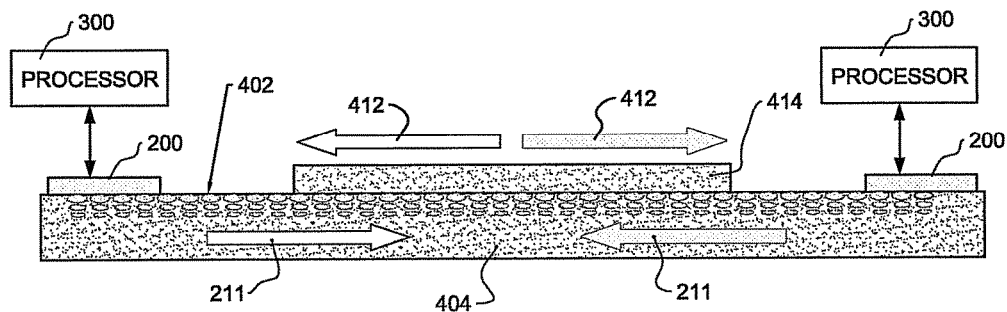
FIG. 28 is an illustration of multiple actuators placed near a wound, and propagating SAW towards the wound 404 results in micro-streaming of the wound liquid in an opposite direction—out of the wound.

Reference is now made to FIG. 28, which is an illustration of multiple actuators 200 placed near wound 404, and propagating SAW towards wound 404 as represented by arrows 211, which results in micro-streaming of the wound liquid 414 in an opposite direction—out of the wound 404, as represented by arrows 412.

In some embodiments, each of the two actuators 200 may operate on a different frequency, which allows for SAW to be created at different depths. These actuators may move the wound biomass in an opposite direction with respect to the direction of SAW propagation. Furthermore, SAW may influence wound healing by providing better distribution of the drugs or healing creams on the surface of the wound and micro-streaming of the wound bio mass out of the wound area.

Figure 29:
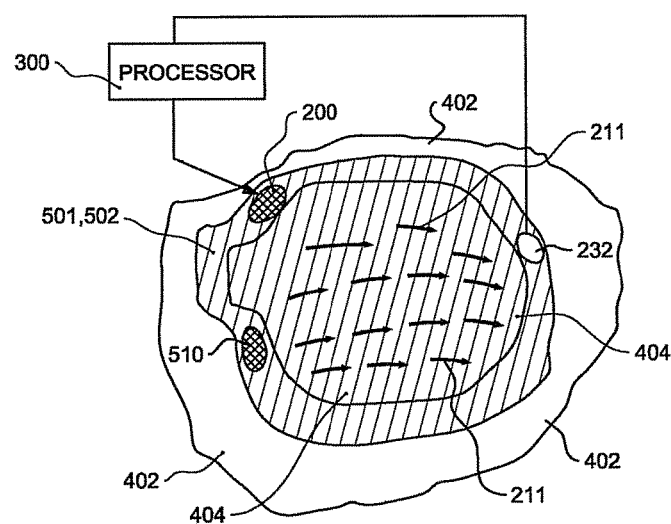
FIG. 29 is a schematic illustration of an acoustic pad for inducing micro-pumping, in accordance with embodiments of the present invention.

Reference is now made to FIG. 29, which is a schematic illustration of an acoustic pad 500 for inducing micro-pumping, in accordance with embodiments of the present invention. Acoustic pad 500 includes a patch 501, wherein the patch 501 has several components either attached thereto on its surface, or sewn into its layers. The components include at least one actuator 200, processor 300, a battery 510, and optionally a sensor 232. Moreover, a wound dressing is spread onto the surface of patch 501.

Vibrations induced via acoustic pad 500 enhance anti-sticking. A direction of SAW propagation is shown by arrows 211. Moreover, when the wound dressing has micro-capillaries, micro-pumping may occur in a central part of the wound due to standing waves. Furthermore, this micro-pumping may induce negative pressure, which can aid in wound healing.

In some embodiments, acoustic pad 500 includes thin capillaries, or suction tubes, through which the wound dressing can directly contact the wound area. The actuators 200 create SAW on the capillaries, wherein the direction of SAW is opposite to the wound liquid movement direction, which due to negative pressure creates suction within the capillaries, causing micro-pumping occur. This obviates the need for vacuum and thus also for sealing of the wound dressing (in order to create the vacuum). In some embodiments, acoustic pad 500 is a disposable patch.

It is known in the art that in operation, damaged tissue may be treated by applying micro-pumping to a wound over an area sufficient to promote the migration of epithelial and subcutaneous tissue toward the wound and for a time period sufficient to facilitate closure of the wound. The active disposable patch is useful for treating pressure sores and preventing diabetic wounds.

The described methods are also suitable for treating a burn wound by applying a negative or reduced pressure to the burn over the surface and for a time sufficient to inhibit progression in the depth of the burn. The method is useful on a partial thickness burn soon after its infliction. One use of this method is its application to a wound for a selected time period such as at least three days to reduce the bacterial density of an infected wound to the point at which surgical closure can be attempted. Another aspect of the invention is a method of enhancing the attachment of adjacent tissue to a wound which comprises applying micro-pumping to a joined complex of the adjacent living tissue and the wound at a sufficient magnitude of micro pumping and for a sufficient time duration to promote the migration of epithelial and subcutaneous tissue toward the complex. This method enhances attachment of adjacent tissue to tissues of the wound edges. Another use of this method is to enhance attachment of an open skin graft to the wound tissue.

Figure 30:
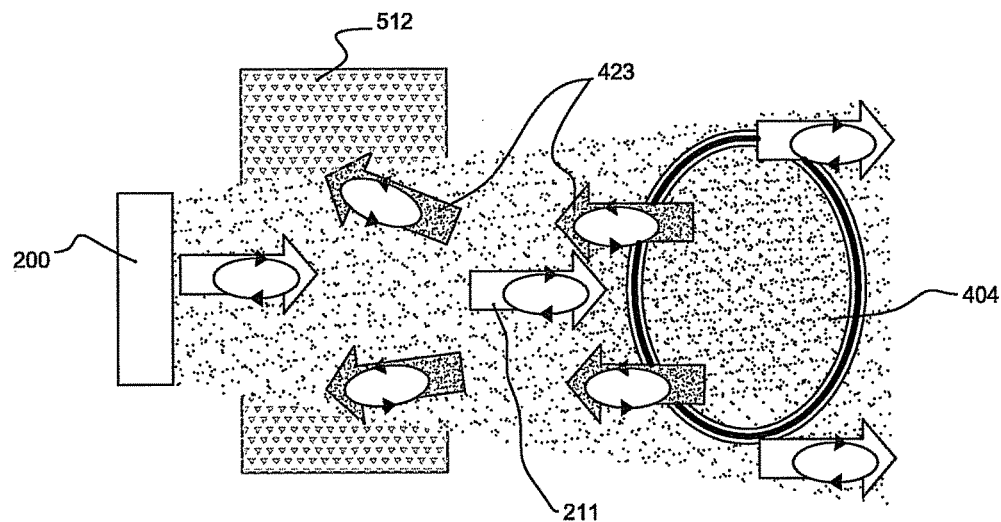
FIG. 30 is a schematic illustration of a system for producing SAW having a dressing material coupler for wound biomass coupling.

Reference is now made to FIG. 30, which is a schematic illustration of a system for producing SAW having gauze or other dressing material coupler 512 for wound biomass coupling. SAW are transmitted through coupler 512, and the wound mass is soaked due to the micro-pumping effect. The wound biomass is configured to move in a direction, shown by arrows 423 which is opposite to the direction of SAW, shown by arrows 211. In some embodiments, two actuators 200 may be used. In some embodiments, each of two actuators 200 may have different intensities and/or frequencies, contributing to a filtration effect, when bio mass particles of different sizes are sucked into opposite directions.

Figure 31:
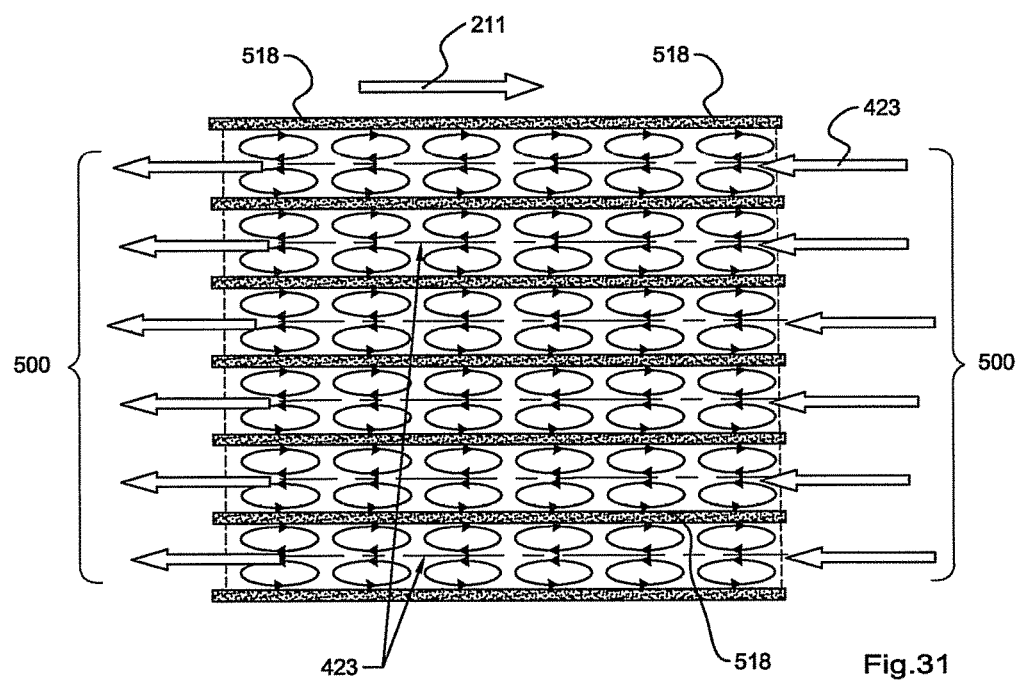
FIG. 31 is a schematic illustration of an acoustic pad having capillaries through which liquid may pass.

Reference is now made to FIG. 31, which is a schematic illustration of acoustic pad 500 having capillaries 518 through which liquid 414 may pass. For example, the wound mass may be pumped away from the wound and/or liquid drugs may be introduced to the wound. Acoustic pad 500 may have a plurality of capillaries 518, and may be comprised of metal, plastic, piezo-electric materials or combinations thereof. In some embodiments, capillaries 518 are themselves the actuators 200. In other embodiments, actuators 200 are attached to capillaries 518 and are miniaturized so as not to interfere with flow of liquid. In addition to SAW excitement, the active capillaries may create wound mass suction in a direction depicted by arrows 423 which is opposite to a direction of SAW propagation, depicted by arrow 211. SAW decrease the Reinold's number of the liquid; therefore the liquid near the capillary walls moves more with respect to the wall of the capillary, preventing bacterial adhesion to the capillary walls. In some embodiments, some capillaries are used for wound mass removal, while other capillaries are simultaneously or non-simultaneously used for delivery of liquid drugs.

Figure 32:
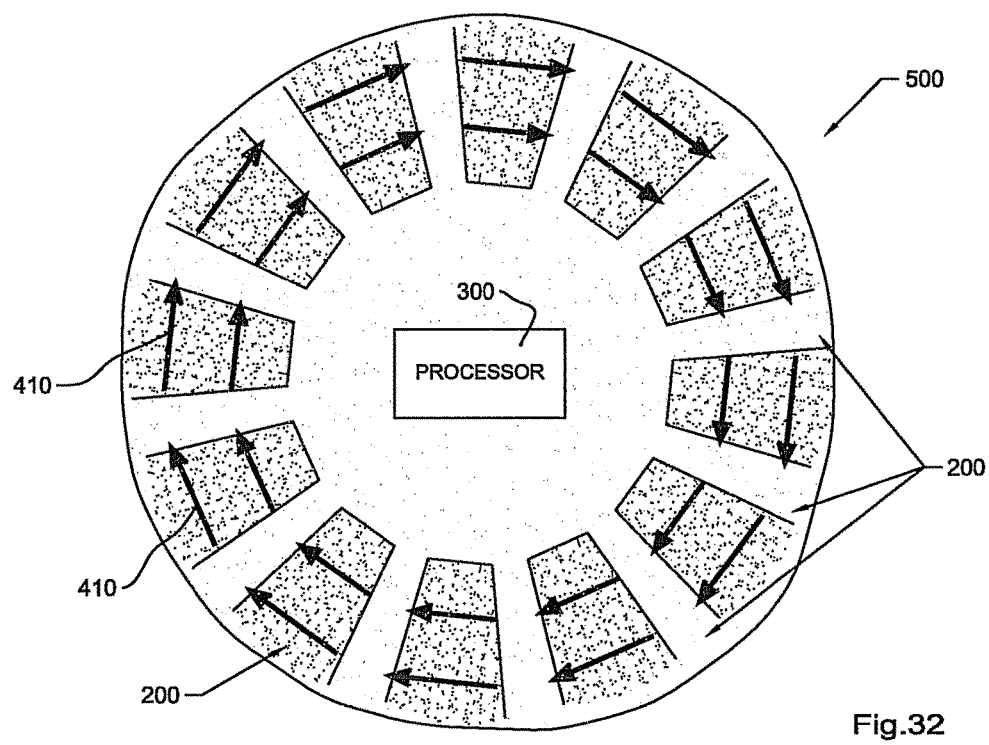
FIG. 32 is an illustration of an active acoustic pad, in accordance with embodiments of the present invention.

Reference is now made to FIG. 32, which is an illustration of an active acoustic pad 500, in accordance with embodiments of the present invention. In the configuration shown in FIG. 32, multiple actuators 200 are arranged in a star-like configuration, with processor 300 positioned in the center. This configuration enables circular propagation of SAW, as depicted by arrows 410. In some embodiments, an actuator 200 may be placed at the center. This configuration enables SAW propagation of running waves from the center to the periphery. The character of the wave propagation may be chosen by a medical professional depending on the phase or condition of wound healing. For example, in the first phase of wound healing it may be desirable to use the configuration described with respect to FIG. 32, wherein a circular SAW propagation is achieved, while in the second wound healing phase, a center to periphery configuration may be desirable. The configuration of capillaries may vary as well. For example, in some embodiments, capillaries 418 may be positioned on two opposing sides of acoustic pad 500, while in other embodiments, capillaries 418 may be positioned around acoustic pad 500. Any suitable configuration of actuators 200 and/or capillaries 418 is possible.

Figure 33:
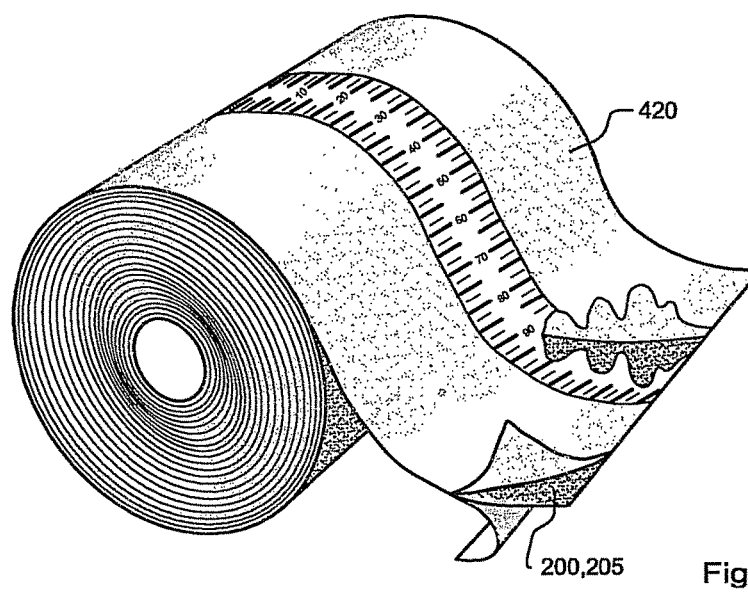
FIG. 33 is an illustration of a wound healing tape, in accordance with embodiments of the present invention.

Reference is now made to FIG. 33, which is an illustration of a wound healing tape 420, in accordance with embodiments of the present invention. Actuators 200 are incorporated into a layer of wound healing tape 420. In some embodiments, incorporated actuators are IDTs 205.

In some embodiments, actuators 200 and sensors 232 are incorporated into acoustic pad 500, both of which are connected to processor 300. Processor 300 may transmit data received from sensors 232 in real time to a computer or a telemedicine system and a medical professional may manage the healing process and regulate healing intensity through commands to processor 300.

4. Methicillin-Resistant *Staphylococcus aureus* Treatment with Saw

Methicillin-resistant *Staphylococcus aureus* (MRSA) is a specific strain of the *Staphylococcus aureus* bacterium that has developed antibiotic resistance to all penicillins, including methicillin and other narrow-spectrum β-lactamase-resistant penicillin antibiotics. Thus MRSA is also sometimes referred to as Oxacillin-resistant *Staphylococcus aureus* (ORSA) and popularly termed a "superbug".

While an MRSA colonization in an otherwise healthy individual is not usually a serious matter, infection with the organism can be life-threatening to patients with deep wounds, intravenous catheters or other foreign-body instrumentation, or as a secondary infection in patients with compromised immune systems. This is partly due to the fact that MRSA does not respond to the antibiotics normally prescribed for the infections in question, and can hence progress unchecked.

Vancomycin and teicoplanin are glycopeptide antibiotics used to treat MRSA infections. These drugs are administered intravenously. Several new strains of the bacterium have been found showing antibiotic resistance even to vancomycin and teicoplanin; those new evolutions of the MRSA bacteria are dubbed "vancomycin intermediate-resistant *Staphylococcus aureus*" (VISA). Linezolid, quinupristin/dalfopristin, daptomycin, tigecycline are more recent additions to the therapeutic arsenal, generally reserved for severe infections which do not respond to glycopeptides. Less severe infections may be treated by oral agents including: linezolid, rifampicin+fusidic acid, pristinamycin, co-trimoxazole (trimethoprim+sulfamethoxazole), doxycycline and clindamycin.

Because cystic fibrosis patients are often treated with multiple antibiotics in hospital settings, they are often colonized with MRSA, potentially increasing the rate of life-threatening MRSA pneumonia in this group. The risk of cross-colonization has led to increased use of isolation protocols among these patients. Out-of-hospital strains of MRSA, now designated as community-acquired, methicillin-resistant *staph. aureus*, or CAMRSA, are not only difficult to treat but are especially virulent. CAMRSA apparently represents a hybrid between MRSA which escaped from the hospital environment and the once easily treatable community organisms. Most of the hybrid strains also acquired a virulence factor which makes their infections invade more aggressively, resulting in deep tissue infections following minor scrapes and cuts, and many cases of fatal pneumonia as well.

The present invention includes treatment of MSRA using SAW. In intravenous devices and implants, SAW is used to fight bacterial infections, and enhance antibiotic efficacy, as well as enhance wound healing and drug delivery.

5. Cosmetics and Anti-Agent Applications

The skin is a multi-layered organ. The stratum corneum (SC)—the outermost layer of the skin—presents the principal resistance to the penetration of topically applied compounds, such that the number of molecules currently used in topical and cosmetic dermal delivery is quite limited. Mild treatment of the skin by ultrasound is a commonly practiced method used by cosmeticians for cosmetic skincare. It is a purpose of the present invention to reduce the appearance of fine lines and wrinkles and/or rapidly lighten photodamaged skin by applying moisture and/or other cosmetic ingredients to the stratum corneum.

SAW actuated devices and disposable patches can address a host of cosmetic and topical concerns, including moisturizing, firming, anti-cellulite, acne, facial redness, sun damage repair. The use of SAW can enhance the permeation of compounds, due to elliptical motion of particles during micro vibration on the surface, and due to micro-streaming resulting therefrom. Thus, micro-electronic skin care products provide a significant increase in the percentage of active cosmetic ingredients that can be delivered onto the upper layers of the skin.

Skin aging includes a slower turnover of the surface skin and slower wound healing. Thinning makes the skin more fragile and vulnerable to damage and more sensitive to irritating environmental factors and allergens. Collagen cross-linking is damaged and as a result, the skin loses much of its strength and elasticity. The moisture holding capacity is decreased and the skin becomes dry and loose. The fat content in the skin is decreased, resulting in a less plump and smoother look. The number of blood vessels in the skin decreases, and the skin loses its youthful color and glow. Anti-aging formulations include anti-wrinkle, de-pigmentation, skin regeneration, and sunspot treatment, among others.

Skin aging results in a slower turnover of the surface skin and slower wound healing. The skin becomes more fragile and vulnerable to damage and more sensitive to irritating environmental factors and allergens. As the moisture holding capacity is decreased, the skin becomes dry and loose, losing its youthful color and glow.

Embodiments of the present invention include a SAW-based electrically driven method to more effectively reduce the appearance of fine lines and wrinkles, leaving the skin feeling silky and smooth for several hours. These methods may further erase signs of fatigue, reduce the appearance of fine lines and wrinkles, diminish the appearance of crow's feet, smooth out and lift skin around the eye contour, deliver extra moisture to the skin, and improve firmness of the eye contour. Activated SAW anti-aging skincare devices may be produced as a hand-held device and/or as disposable patches, as well as in a variety of shapes for different application areas.

Hyper-pigmentation and melasma are common skin disorders, predominantly affecting the faces of women. It appears as symmetrical hyper-pigmented maculae, which can be confluent or punctuate. The cheeks, upper lip, chin, and forehead are the most common locations, but it can occasionally occur in other sun-exposed locations. The treatment of hyper-pigmented skin is still quite unsatisfactory, as indicated in cosmetic scientific literature. Thus, there is a clear need to develop new, safe skin lightening systems, which will provide desirable alleviation of hyper-pigmentation.

SAW activated devices and patches can enhance delivery of a wide variety of skin and spot whitening molecules, thus enhancing the power of common skin whitening cosmetic ingredients, the decrease of hyper-pigmentation skin discoloration, sun, and age spots significantly faster than ordinary cosmetic creams alone.

Figure 34:
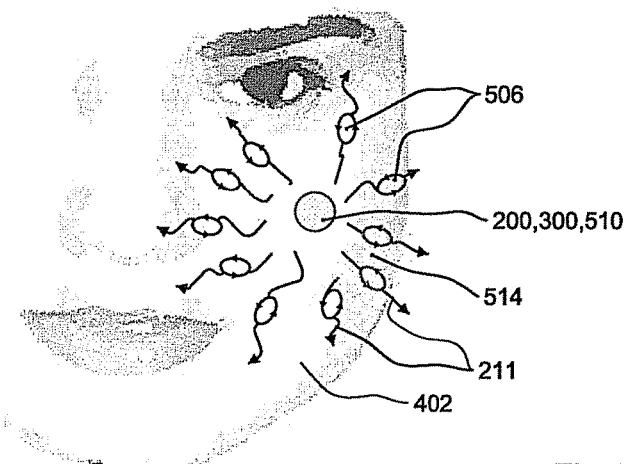
FIG. 34 is an illustration of a flexible patch for cosmetic treatment.

Reference is now made to FIG. 34, which is an illustration of a flexible patch 514 for cosmetic treatment. Flexible patch 514 includes SAW actuators 200, with a processor 300 and at least one battery 510 incorporated therein, and may be attached to the facial skin 402. The depth of SAW propagation may be managed by varying the wave frequency. Battery 510 is configured to provide energy in the range of 5-20 mW/cm$^2$, and processor 300 may be configured to control one or more actuators 200 simultaneously. Processor 300 may act in accordance with a predetermined program, and may control simultaneously one or more patches.

In some embodiments, actuator 200 distributes the waves continuously as shown by arrows 211 and ellipses 506. In some embodiments, actuator 200 distributes SAW in one direction, and SAW may be absorbed and reflected due to energy absorbers such as gauze, synthetic porous materials, gum, and the like, which can prevent them from being propagated in other directions. In some embodiments, flexible patch 514 includes multiple actuators, controllers and batteries, each of which is a system which can operate independently. Propagation of running SAW in several directions can result in standing waves in an overlapping area. This may provide a more focused acoustic energy treatment. In some embodiments, actuator 200 is ring-shaped, or multiple actuators 200 may be circularly arranged. This configuration allows for standing waves to be created in the center portion, thus concentrating acoustic pressure and creating a micro-cavitation effect. The cavitation creates momentum temperature increasing to about 70° C. The described ring or circular actuator construction may be applied for acne healing, or for any other condition wherein high energy may be useful.

Figure 35:
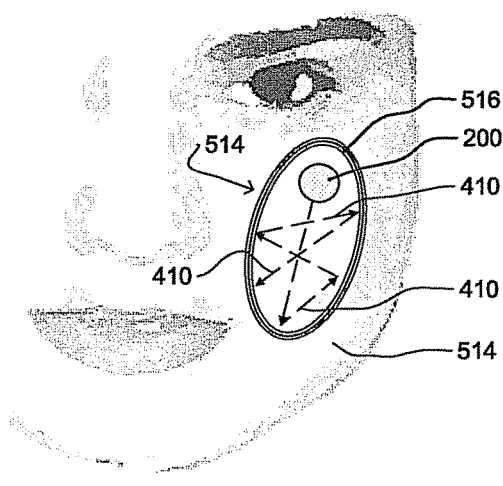
FIG. 35 is an illustration of a flexible patch having an absorbing material at its edges for reflecting waves.

Reference is now made to FIG. 35, which is an illustration of flexible patch 514, in accordance with embodiments of the present invention. Flexible patch 514 is relatively large (in a range of about 1-50 cm$^2$), while actuator 200 is relatively small (in a range of about 0.5-3 cm$^2$). Flexible patch 514 further includes an absorbing material 516 at its edges, which can reflect waves. Thus, a chaotic SAW effect may be achieved on the area treated by flexible patch 514. The chaotic directions of SAW are illustration by arrows 410.

In some embodiments, sensors 232 may be incorporated into flexible patch 514 or be placed nearby. Sensors may measure parameters such as skin parameters, velocity of the acoustic wave in the skin, elasticity of skin, temperature, humidity, etc. SAW may provide micro-massage which may be a preventive action for anti aging.

In some embodiments, flexible patch 514 includes multiple actuators 200. An active cosmetic agent, such as a cream, is applied to the skin in an area near the attached flexible patch 514. SAW are propagated into the cosmetic agent, activating chemical components and causing specific distributions of the cosmetic agent. The process may be managed due to feedback obtain from sensors 232. In some embodiments, flexible patch 514 also includes a biologically active component, either in liquid or cream form, or as a slow-release component of patch 514. Micro streaming and micro pumping due to SAW may result in increased activity of these active components on skin, thus reducing healing time increasing efficacy. Other possible constructions of patches may be produced similar to the ones described above with respect to wound healing.

Figure 36:
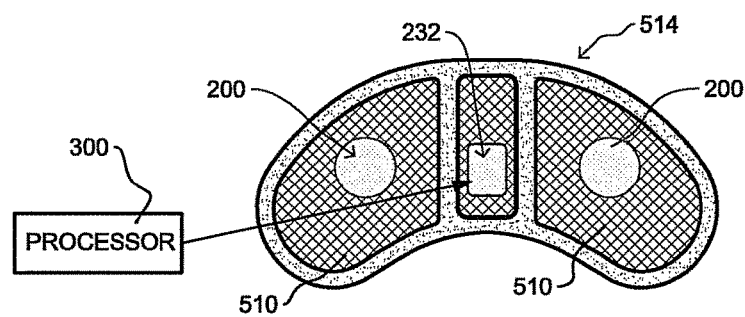
FIG. 36 is an illustration of a flexible patch having an arch-like configuration.

Reference is now made to FIG. 36, which is an illustration of flexible patch 514, in accordance with embodiments of the present invention. As shown in FIG. 36, an arch-like configuration may include a first side and a second side. An actuator 200 is included on each side, with a sensor 232 positioned in the middle. A battery 510 or multiple batteries are incorporated as well. In some embodiments, a thin flexible battery such as those available from Power Paper, Nec or Solicore companies may be used. Flexible patch 514 includes an adhesive layer, with a protective layer which can be removed prior to adhesion. In some embodiments, a switch may be included on the protective layer, wherein by removing the protective layer, the battery of the patch is activated.

Figure 37A:
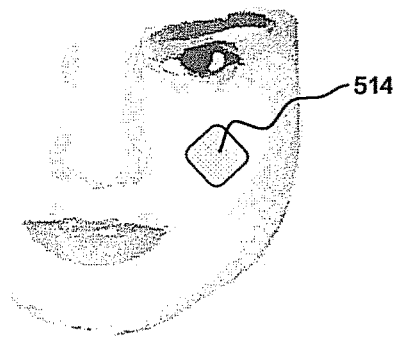
FIGS. 37A-37D are illustrations showing various shapes and configurations of a patch.
Figure 37B:
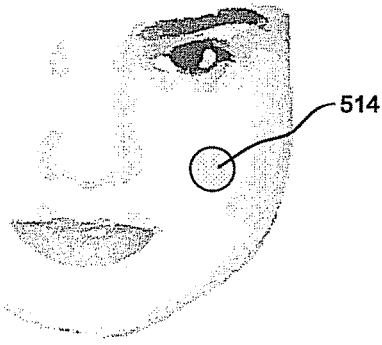
Figure 37C:
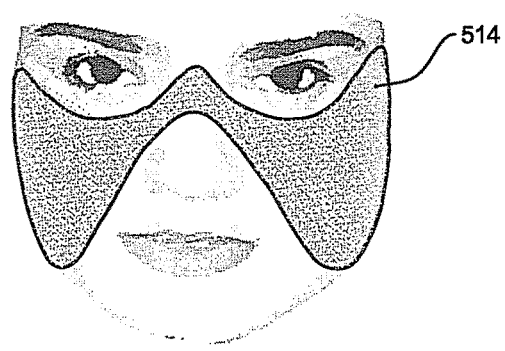
Figure 37D:
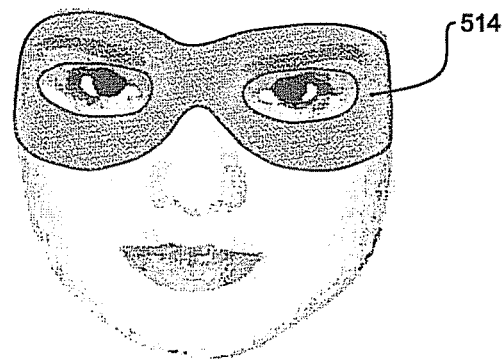

Reference is now made to FIGS. 37A-37D, which are illustrations showing various shapes and configurations of patch 514. Flexible patch 514 may be elongated, as shown in FIG. 37A, circular, as shown in FIG. 37B, configured to fit on the cheek portions of the face, as depicted in FIG. 37C, configured in an eye-mask configuration, as shown in FIG. 37D, or in any other shape or configuration. Patch 514 may be applied to one or both facial sides and may have long action time, for example overnight, or may have short action times, on the order of minutes.

Reference is now made to FIG. 38, which is an illustration of a hand-held cosmetic device 518, in accordance with embodiments of the present invention. An actuator 200 comprised of a thin piezo-electric plate is placed at a contact portion 530 of cosmetic device 518. Contact portion 530 is a portion which is placed against the facial skin during treatment. Actuator 200 is comprised of a metallic layer and a piezoelectric layer with an electrode thereon. Metallic layer is positioned outward, such that contact with the skin will be made via metallic layer. A processor 300 and a battery 510 are placed within a handle 532 of cosmetic device 518. Actuator is electrically connected to processor 300 and battery 510. Actuator 200 may have a dual-function mode: micro massaging action under the attachment surface and running surface acoustic waves excitement spread around the actuator, for example, as shown by arrows 211.

The following are the parameters of cosmetic device 518:
1. On the surface beyond the active actuator, acoustic energy parameters are:
Spatial average, temporal average intensity: $I_{SATA}$=10 mW/Cm$^2$
Spatial peak, temporal average intensity: $I_{SPTA}$=55 mW/cm$^2$
2. The actuator produces SAW surrounding the device active plate. This is an advantageous feature of SAW—their ability to spread on surfaces. These SAW are transmitted around the surface at a predetermined depth corresponding to the distance A as it relates to the SAW wavelength. The acoustic energy dissipates distancing from the active disc.

Reference is now made to FIG. 39, which is an illustration of a tube 520 of cream. In embodiments of the present invention, actuator 200, processor 300 and battery 510 are all incorporated within a cover 522. Actuator 200 causes SAW on the cover surface and on the tube surfaces, as shown by arrows 211. The activated surfaces may be attached to the desired surface, for example to the face. Therefore facial micro massage or deeper cream penetration may be achieved. In some embodiments, actuator 200 with processor 300 and battery 510 are completely incorporated into cover 522. In other embodiments, actuator 200 is a ring-shaped actuator and covers a portion of cover 522, creating focused waves in the center. In yet other embodiments, actuator 200 may be positioned such that acoustic power causes more effective cream to be pushed out of tube 520. In some embodiments, one or more actuators 200 may be incorporated into cleaning sticks, which may be used as a cosmetic accessory.

6. Pain Treatment: Post Operative, Women after 65, Women Menstrual Pain, Sportsmen Chronic or recurrent pain has been treated with a variety of relief methods—ranging from medications to heating pads or ice packs to less prevalent methods such as massage therapy, seeing a chiropractor, or homeopathic and herbal remedies. However, most of these methods, including drugs and home remedies, fall short. Reference is now made to FIG. 40, illustrating active pain relief patches 524, in embodiments of the present invention. Pain relief patches 524 include a base material and an adhesive layer, with one or more thin plate type piezo-electric actuators incorporated into the base material. A separate processor 300 may be provided, wherein processor 300 is in electrical communication with actuators 200.

In some embodiments, the piezo-element actuator may be a piezo bender, and may consist of thin piezo material layer glued to a thin metallic plate. The piezo-element is incorporated into the patch base material in such a manner that the metallic plate faces outward with respect to the skin, and the piezo material plus the adhesive layer of the patch face inward with respect to the skin. When activated by processor 300, actuators 200 create standing wave on the metallic surfaces. These standing waves penetrate into the depths of the skin layers, resulting in pain relief effect due to enhanced diathermy effect. Furthermore, the standing wave is a generator of SAW on the areas surrounding the actuator surfaces, which enhance biological processes (blood flow, liquid and gas exchange, and etc.) further resulting in pain relief.

In some embodiments the pain relief patch 524 may include a drug layer component (liquid, cream or slow release component of the patch). Micro streaming and micro pumping due to SAW may result in increased activity of these active components, thus decreasing pain relief time and increasing efficacy. Other possible constructions may have a processor 300 in chip configuration, thus allowing it to be incorporated into the patch. Pain relief patch 524 may be a disposable device, or in a pad configuration for repeatable use. A hand-held device for pain relief may have the same components incorporated in a plastic hand held device, and may have one or more acoustic intensity levels.

7. Experimental Results. Enhanced Cosmetic Agent and Drug Delivery Ex-Vivo

Researchers apply ultrasound to targeted drug delivery through a process called sonophoresis. This technique uses sound waves instead of needles to inject drugs such as insulin and interferon directly through the skin. The high-frequency waves open tiny holes in cell membranes, which make the cells temporarily permeable in localized areas and allow for better penetration of the drug into the blood vessels below the skin. This enhances drug effectiveness, reduces dosage requirements and toxicity, and allows clinicians to deliver drugs to specific areas in the body for localized treatment. The mechanisms by which ultrasound augments these effects are only partially understood. It is known that ultrasound causes biophysical reactions producing hydroxyl radicals, combinations of hydrogen and oxygen atoms that in turn affect cell membranes. Furthermore, there have been some investigations on the use of low-level ultrasound to enhance the effects of chemotherapy on localized tumors. This may trigger cellular responses that could interact with chemotherapeutic drugs. The microbubble motion produced by ultrasound in fluids could also cause stresses in cell membranes, thus altering the activity of genes that control important processes affecting the action of the drugs. One of the first applications of ultrasound-enhanced drug delivery is to dissolve life-threatening blood clots. Another possibility is to inject drugs through a catheter using low-energy, localized ultrasound to direct the drug to the targeted site in the body.

Thus, an ex-vivo experiment was conducted to test SAW effectiveness in penetrating liquid molecules into skin layers. Permeability of dye was investigated using guinea pig skin and Trypan Blue stain. Briefly, the skin was clipped free from hair and a hand-held device such as cosmetic device 518 depicted in FIG. 38 having a SAW actuator thereon, was brought into contact with skin so as to face the hair side. The dye was interposed between the PZT element and the skin. An energy of $I_{SPTA}$=55 mW/cm$^2$ was applied for 20 minutes. Transverse cuts of both skin examples (activated and control) revealed penetration of dye into guinea pig skin as a result of exposure to SAW.

Additional pre-clinical experiments have shown that SAW waves provide more efficient pain relief in women, elderly people and sportsmen in comparison to conventionally used physiotherapy (such as ultrasound combined with paraffin bath), when the pain source is near the skin surface. The treatment of Achilles pain, hand osteoporosis, and menstrual pain were tested proving pain relief in all these cases resulting in SAW applicators use.

8. SAW Enhanced Bio Effects

1. SAW enhance movement of stagnating fluids of various etiologies and impairs the microcirculation. The statement was proved theoretically and experimentally. The effect may be employed for example to improve gas exchanges and the maintenance of the homeostasis.

2. SAW able to exert motion of objects be they natural or artificial or a combination of both, due to energy conduction.

3. Use of microvibrations for increment of exchanges at interfaces. The surface area is dynamically "increased" resulting increment of gas, nutrients, fluid and heat exchange.

4. Inhibition of adhesion formation following surgery through specific targeted SAW vibrations to affected area 5. Micro steaming, micro pumping and draining of fluid along surfaces by using SAW 6. Improvement of flow in thin tubes due to boundary layer effect 7. Tropic effect upon selected structures or areas due to stimulation and micromotion of cells and through enhanced exchanges of oxygen, nutrients and disposal of waste material.

8. Resist crystallization, resist formation of thrombus, resist tissue in-growth due to obtained hydrophobic properties 9. Activation of drugs and biomaterials due to interaction of SAW with biomaterials and drugs While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A method for treating human skin, the method comprising:
   positioning a piezo bender actuator on the skin, wherein said actuator is comprised of piezoelectric material glued to a metallic plate;
   electrically connecting said actuator to a processor;
   activating said actuator via said processor, thereby enabling said actuator to vibrate in natural bending vibration modes;
   said vibrating actuator producing surface acoustic waves in the form of running waves on the skin around the actuator and wherein said producing causes skin particles to move elliptically; and wherein the distance between two maximal amplitudes of said bending vibration modes are proportional to a half wave length of said surface acoustic waves produced on the skin; and
   controlling parameters of said activating so as to achieve particular treatment effects on the skin by said produced surface acoustic waves.

2. The method of claim 1, wherein said producing comprises producing surface acoustic waves at an interface between the skin and a therapeutic agent.

3. The method of claim 1, wherein said activating comprises activating the actuator to vibrate in a mode selected from: Lamb symmetrical, Lamb antisymmetrical and natural vibration.

4. The method of claim 1, wherein said controlling comprises selecting a frequency.

5. The method of claim 1, wherein said controlling comprises selecting an amplitude.

6. The method of claim 5, wherein said amplitude is in a range of 1 nanometer to 50 microns.

7. The method of claim 1, wherein said actuator having a shape selected from the group consisting of: a plate, a disk, a ring, a shell, a string, and a strip.

8. The method of claim 1, wherein said controlling comprises controlling a depth of surface acoustic waves.

9. The method of claim 8, wherein said depth is between 1-2 wavelengths of the produced surface acoustic waves.

10. The method of claim 1, wherein said controlling comprises providing an acoustic power range of up to 0.1 W/cm$^2$.

11. The method of claim 1, further comprising providing an additional electrical input to produce an electric-acoustic effect.

12. The method of claim 11 wherein said additional electrical input is selected from the group consisting of: continuous direct electric current (DC), radio frequency (RFC), alternating electric current (AC), and laser.

13. The method of claim 1, wherein said positioning a piezo bender actuator comprises positioning multiple actuators on the skin in a circular configuration so as to produce a focused effect of surface acoustic waves on the skin.

14. The method of claim 13, wherein said particular treatment effects include destruction of tumor cells.

15. The method of claim 1, wherein said positioning a piezo bender actuator comprises providing an actuator comprised of a ring-shaped piezo-element, and wherein said producing comprises producing a standing wave at a center of said ring-shaped piezo-element.

16. The method of claim 1, wherein said producing surface acoustic waves causes inhibition of bacterial biofilm due to bacterial relative velocity, wherein vibration amplitudes are smaller than a Z-potential repulsive zone.

17. The method of claim 1, wherein said particular treatment effects are selected from the group consisting of inhibiting particle attachment to the skin, inhibiting adhesion, inhibiting growth and aggregation of cells into micro colonies, and maturation and dissemination of progeny cells for new colony formation.

18. The method of claim 1, wherein said producing comprises producing surface acoustic waves in one direction, and wherein said producing results in movement of particles and bacteria in a direction which is opposite to said one direction.

19. The method of claim 1, wherein said particular treatment effects are selected from the group consisting of: micro massage, healing processes, tissue fluid interchange, increased growth of capillary, increased pH of tissue liquids, and lowered pain syndrome, from the group consisting of: micro streaming, deep penetration of liquid placed on the skin, and homogenization of cream particles from a cream placed on the skin, or from the group consisting of: resistance of thrombus formation, resistance to tissue in-growth, enhanced drug administering, adhesion, non-adhesion, friction, potency, anti-biofouling, the cleansing of tissue, the removal of necrotic debris, disinfection, the "biostimulation" of cells, blood flow, micromassaging, removal of burn wound bandages, and drying.

20. The method of claim 1, further comprising providing a bandage, and wherein said producing comprises producing surface acoustic waves at an interface between the skin and said bandage.

21. A device for treatment of skin, the device comprising:
   a skin-contacting portion;
   a piezo bender actuator incorporated into said skin-contacting portion, wherein said actuator is comprised of piezoelectric material glued to a metallic plate, and a processor for controlling said actuator to vibrate in one or more natural bending vibration modes to produce surface acoustic waves in the form of running waves on the skin around the actuator and wherein said producing causes skin particles to move elliptically; and wherein the distance between two maximal amplitudes of said bending vibration modes are proportional to a half wave length of said surface acoustic waves produced on the skin.

22. The device of claim 21, wherein said skin-contacting portion is a patch.

23. The device of claim 22, wherein said patch is configured to be placed at a wound site.

24. The device of claim 22, wherein said patch is configured to be placed at an insertion site for a catheter.

25. The device of claim 22, wherein said patch comprises a permeable layer and wherein a disinfecting agent is introduced into the skin through the permeable layer, and wherein said produced surface acoustic waves enhance permeability of the skin to the disinfecting agent.

26. The device of claim 21, wherein the device is a hand-held device and said skin-contacting portion is an end of said hand-held device.

27. The device of claim 21, wherein said skin-contacting portion is a glove.

28. The device of claim 27, wherein said glove comprises a permeable layer and wherein a disinfecting agent is introduced into the skin through the permeable layer, and wherein said produced surface acoustic waves enhance permeability of the skin to the disinfecting agent.

29. The device of claim 21, wherein said actuator is of a configuration selected from the group consisting of: a plate, a disk, a ring, a shell, a string, and a strip.

30. The device of claim 29, wherein said actuator produces tension and repulsion of skin particles.

31. The device of claim 29, wherein said produced surface acoustic waves are configured to provide treatment, the treatment selected from the group consisting of: anti-aging, skin lightening, micro massage, cosmetic agent penetration and acne treatment.

32. The device of claim 21, further comprising a bioactive coating.

33. The device of claim 21, further comprising a sensor incorporated into said skin-contacting portion.

34. The device of claim 33, wherein said processor is configured to adjust output parameters based on feedback from said sensor.

* * * * *